US009023601B2

(12) United States Patent
Oleinikov

(10) Patent No.: US 9,023,601 B2
(45) Date of Patent: *May 5, 2015

(54) MICROARRAY SYNTHESIS AND ASSEMBLY OF GENE-LENGTH POLYNUCLEOTIDES

(75) Inventor: Andrew V. Oleinikov, Mill Creek, WA (US)

(73) Assignee: Gen9, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/250,207

(22) Filed: Sep. 30, 2011

(65) Prior Publication Data
US 2012/0270750 A1 Oct. 25, 2012

Related U.S. Application Data

(63) Continuation of application No. 12/488,662, filed on Jun. 22, 2009, now Pat. No. 8,058,004, which is a continuation of application No. 10/243,367, filed on Sep. 12, 2002, now Pat. No. 7,563,600.

(51) Int. Cl.
C12Q 1/68 (2006.01)
C12P 19/34 (2006.01)
(Continued)

(52) U.S. Cl.
CPC ............ C40B 50/14 (2013.01); B01J 19/0046 (2013.01); B01J 2219/00378 (2013.01); B01J 2219/00385 (2013.01); B01J 2219/00432 (2013.01); B01J 2219/00454 (2013.01); B01J 2219/005 (2013.01); B01J 2219/00527 (2013.01); B01J 2219/00585 (2013.01); B01J 2219/00596 (2013.01); B01J 2219/00605 (2013.01); B01J 2219/00626 (2013.01); B01J 2219/00639 (2013.01); B01J 2219/00641 (2013.01); B01J 2219/00659 (2013.01); B01J 2219/00675 (2013.01); B01J 2219/00677 (2013.01);
(Continued)

(58) Field of Classification Search
CPC ...... B01J 19/00; B01J 19/0046; C12Q 1/6844
See application file for complete search history.

(56) References Cited

U.S. PATENT DOCUMENTS 4,683,195 A 7/1987 Mullis
4,683,202 A 7/1987 Mullis
(Continued)

FOREIGN PATENT DOCUMENTS

EP 0259160 3/1988
EP 1015576 3/1999
(Continued)

OTHER PUBLICATIONS

Adessi et al., "Solid phase DNA amplification: characterisation of primer attachment and amplification mechanisms," Nucleic Acids Research, 28(20):E87, (Oct. 15, 2000).
(Continued)

Primary Examiner — Young J Kim
(74) Attorney, Agent, or Firm — Greenberg Traurig, LLP; Natalie Salem

(57) ABSTRACT

There is disclosed a process for in vitro synthesis and assembly of long, gene-length polynucleotides based upon assembly of multiple shorter oligonucleotides synthesized in situ on a microarray platform. Specifically, there is disclosed a process for in situ synthesis of oligonucleotide fragments on a solid phase microarray platform and subsequent, "on device" assembly of larger polynucleotides composed of a plurality of shorter oligonucleotide fragments.

18 Claims, 14 Drawing Sheets

(51) Int. Cl.
    *C07H 21/02*     (2006.01)
    *C07H 21/04*     (2006.01)
    *C40B 50/14*     (2006.01)
    *B01J 19/00*     (2006.01)
    *B82Y 30/00*     (2011.01)
    *C40B 80/00*     (2006.01)
    *C40B 40/06*     (2006.01)

(52) U.S. Cl.
    CPC ............ *B01J2219/00689* (2013.01); *B01J 2219/00713* (2013.01); *B01J 2219/00722* (2013.01); *B82Y 30/00* (2013.01); *C40B 40/06* (2013.01); *C40B 80/00* (2013.01)

(56) References Cited

U.S. PATENT DOCUMENTS

| | | | |
|---|---|---|---|
| 4,689,405 A | 8/1987 | Frank | |
| 4,800,159 A | 1/1989 | Mullis | |
| 4,965,188 A | 10/1990 | Mullis | |
| 4,999,294 A | 3/1991 | Looney | |
| 5,104,789 A | 4/1992 | Permar | |
| 5,104,792 A | 4/1992 | Silver | |
| 5,132,215 A | 7/1992 | Jayarama | |
| 5,143,854 A | 9/1992 | Pirrung | |
| 5,356,802 A | 10/1994 | Chandrasegaran | |
| 5,405,783 A | 4/1995 | Pirrung | |
| 5,424,186 A | 6/1995 | Fodor | |
| 5,436,150 A | 7/1995 | Chandrasegaran | |
| 5,436,327 A | 7/1995 | Southern | |
| 5,445,934 A | 8/1995 | Fodor | |
| 5,459,039 A | 10/1995 | Modrich | |
| 5,474,796 A | 12/1995 | Brennan | |
| 5,498,531 A | 3/1996 | Jarrell | |
| 5,605,793 A | 2/1997 | Stemmer | |
| 5,624,711 A | 4/1997 | Sundberg | |
| 5,641,658 A | 6/1997 | Adams | |
| 5,653,939 A | 8/1997 | Hollis | |
| 5,674,742 A | 10/1997 | Northrup | |
| 5,679,522 A | 10/1997 | Modrich | |
| 5,695,940 A | 12/1997 | Drmanac | |
| 5,700,637 A | 12/1997 | Southern | |
| 5,700,642 A | 12/1997 | Monforte | |
| 5,702,894 A | 12/1997 | Modrich | |
| 5,739,386 A | 4/1998 | Holmes | |
| 5,750,335 A | 5/1998 | Gifford | |
| 5,766,550 A * | 6/1998 | Kaplan et al. ............. | 422/68.1 |
| 5,780,272 A | 7/1998 | Jarrell | |
| 5,795,714 A | 8/1998 | Cantor | |
| 5,830,655 A | 11/1998 | Monforte | |
| 5,834,252 A | 11/1998 | Stemmer | |
| 5,858,754 A | 1/1999 | Modrich | |
| 5,861,482 A | 1/1999 | Modrich | |
| 5,871,902 A | 2/1999 | Weininger | |
| 5,877,280 A | 3/1999 | Wetmur | |
| 5,916,794 A | 6/1999 | Chandrasegaran | |
| 5,922,539 A | 7/1999 | Modrich | |
| 5,928,905 A | 7/1999 | Stemmer | |
| 5,929,208 A | 7/1999 | Heller | |
| 5,942,609 A | 8/1999 | Hunkapiller | |
| 5,953,469 A | 9/1999 | Zhou | |
| 6,013,440 A * | 1/2000 | Lipshutz et al. ............. | 506/7 |
| 6,017,696 A | 1/2000 | Heller | |
| 6,093,302 A | 7/2000 | Montgomery | |
| 6,103,463 A | 8/2000 | Chetverin | |
| 6,136,568 A | 10/2000 | Hiatt | |
| 6,150,102 A | 11/2000 | Mills | |
| 6,150,141 A | 11/2000 | Jarrell | |
| 6,165,793 A | 12/2000 | Stemmer | |
| 6,242,211 B1 | 6/2001 | Peterson | |
| 6,248,521 B1 | 6/2001 | VanNess | |
| 6,261,797 B1 | 7/2001 | Sorge | |
| 6,271,957 B1 | 8/2001 | Quate | |
| 6,277,632 B1 | 8/2001 | Harney | |
| 6,280,595 B1 | 8/2001 | Montgomery | |
| 6,284,463 B1 | 9/2001 | Hasebe | |
| 6,287,825 B1 | 9/2001 | Weissman | |
| 6,287,861 B1 | 9/2001 | Stemmer | |
| 6,291,242 B1 | 9/2001 | Stemmer | |
| 6,315,958 B1 | 11/2001 | Singh-Gasson | |
| 6,322,971 B1 | 11/2001 | Chetverin | |
| 6,333,153 B1 | 12/2001 | Fishel | |
| 6,346,399 B1 | 2/2002 | Weissman | |
| 6,358,712 B1 | 3/2002 | Jarrell | |
| 6,365,355 B1 | 4/2002 | McCutchen-Maloney | |
| 6,372,434 B1 | 4/2002 | Weissman | |
| 6,372,484 B1 | 4/2002 | Ronchi | |
| 6,375,903 B1 | 4/2002 | Cerrina | |
| 6,406,847 B1 | 6/2002 | Cox | |
| 6,410,220 B1 | 6/2002 | Hodgson et al. | |
| 6,426,184 B1 | 7/2002 | Gao | |
| 6,444,111 B1 | 9/2002 | Montgomery | |
| 6,444,175 B1 | 9/2002 | Singh-Gasson | |
| 6,480,324 B2 | 11/2002 | Quate | |
| 6,489,146 B2 | 12/2002 | Stemmer | |
| 6,495,318 B2 | 12/2002 | Harney | |
| 6,506,603 B1 | 1/2003 | Stemmer | |
| 6,521,427 B1 | 2/2003 | Evans | |
| 6,534,271 B2 | 3/2003 | Furste | |
| 6,537,776 B1 | 3/2003 | Short | |
| 6,586,211 B1 | 7/2003 | Stahler | |
| 6,605,451 B1 | 8/2003 | Marmaro | |
| 6,613,581 B1 | 9/2003 | Wada | |
| 6,632,641 B1 | 10/2003 | Brennan | |
| 6,650,822 B1 | 11/2003 | Zhou | |
| 6,664,112 B2 | 12/2003 | Mulligan | |
| 6,670,127 B2 | 12/2003 | Evans | |
| 6,670,605 B1 | 12/2003 | Short | |
| 6,897,025 B2 | 5/2005 | Cox | |
| 6,921,818 B2 | 7/2005 | Sproat | |
| 6,969,587 B2 | 11/2005 | Taylor | |
| 6,969,847 B2 | 11/2005 | Davis | |
| 7,179,423 B2 | 2/2007 | Bohm | |
| 7,183,406 B2 | 2/2007 | Belshaw | |
| 7,262,031 B2 | 8/2007 | Lathrop | |
| 7,273,730 B2 | 9/2007 | DuBreuil | |
| 7,303,872 B2 | 12/2007 | Sussman | |
| 7,323,320 B2 * | 1/2008 | Oleinikov ............... | 435/91.5 |
| 7,399,590 B2 | 7/2008 | Piepenburg | |
| 7,432,055 B2 | 10/2008 | Pemov | |
| 7,563,600 B2 * | 7/2009 | Oleinikov ............... | 435/91.1 |
| 8,058,004 B2 * | 11/2011 | Oleinikov ............... | 435/6.1 |
| 2001/0031483 A1 | 10/2001 | Sorge | |
| 2001/0049125 A1 | 12/2001 | Stemmer | |
| 2002/0012616 A1 | 1/2002 | Zhou | |
| 2002/0058275 A1 | 5/2002 | Fishel | |
| 2002/0127552 A1 | 9/2002 | Church | |
| 2002/0132259 A1 | 9/2002 | Wagner | |
| 2002/0132308 A1 | 9/2002 | Liu | |
| 2002/0133359 A1 | 9/2002 | Brown | |
| 2003/0017552 A1 | 1/2003 | Jarrell | |
| 2003/0044980 A1 | 3/2003 | Mancebo | |
| 2003/0050437 A1 | 3/2003 | Montgomery | |
| 2003/0050438 A1 | 3/2003 | Montgomery | |
| 2003/0054390 A1 | 3/2003 | Crameri | |
| 2003/0068643 A1 | 4/2003 | Brennan | |
| 2003/0082630 A1 | 5/2003 | Kolkman | |
| 2003/0087298 A1 | 5/2003 | Green | |
| 2003/0091476 A1 | 5/2003 | Zhou | |
| 2003/0099952 A1 | 5/2003 | Green | |
| 2003/0118485 A1 | 6/2003 | Singh-Gasson | |
| 2003/0118486 A1 | 6/2003 | Zhou | |
| 2003/0120035 A1 | 6/2003 | Gao | |
| 2003/0134807 A1 | 7/2003 | Hardin | |
| 2003/0143550 A1 | 7/2003 | Green | |
| 2003/0143724 A1 | 7/2003 | Cerrina | |
| 2003/0175907 A1 | 9/2003 | Frazer | |
| 2003/0186226 A1 * | 10/2003 | Brennan et al. ............. | 435/6 |
| 2003/0198948 A1 | 10/2003 | Stahler | |
| 2003/0215837 A1 | 11/2003 | Frey | |
| 2003/0215855 A1 | 11/2003 | Dubrow | |
| 2003/0215856 A1 | 11/2003 | Church | |
| 2004/0002103 A1 | 1/2004 | Short | |
| 2004/0005673 A1 | 1/2004 | Jarrell | |

(56) References Cited

U.S. PATENT DOCUMENTS

| | | |
|---|---|---|
| 2004/0009520 A1 | 1/2004 | Albert |
| 2004/0014083 A1 | 1/2004 | Yuan |
| 2004/0101444 A1 | 5/2004 | Sommers |
| 2004/0101894 A1 | 5/2004 | Albert |
| 2004/0101949 A1 | 5/2004 | Green |
| 2004/0110211 A1 | 6/2004 | McCormick |
| 2004/0110212 A1 | 6/2004 | McCormick |
| 2004/0126757 A1 | 7/2004 | Cerrina |
| 2004/0132029 A1 | 7/2004 | Sussman |
| 2004/0166567 A1 | 8/2004 | Santi |
| 2004/0241655 A1 | 12/2004 | Hwang |
| 2004/0259146 A1 | 12/2004 | Friend |
| 2005/0053997 A1 | 3/2005 | Evans |
| 2005/0069928 A1 | 3/2005 | Nelson |
| 2005/0106606 A1 | 5/2005 | Parker |
| 2005/0118628 A1 | 6/2005 | Evans |
| 2005/0227235 A1 | 10/2005 | Carr |
| 2005/0255477 A1 | 11/2005 | Carr |
| 2006/0008833 A1 | 1/2006 | Jacobson |
| 2006/0127920 A1 | 6/2006 | Church |
| 2006/0127926 A1 | 6/2006 | Belshaw |
| 2006/0160138 A1 | 7/2006 | Church |
| 2006/0194214 A1 | 8/2006 | Church |
| 2007/0231805 A1 | 10/2007 | Baynes |
| 2008/0300842 A1 | 12/2008 | Govindarajan |

FOREIGN PATENT DOCUMENTS

| | | |
|---|---|---|
| EP | 1159285 | 9/2000 |
| EP | 1180548 | 2/2002 |
| WO | WO 90/00626 | 1/1990 |
| WO | WO 93/17126 | 9/1993 |
| WO | WO 94/18226 | 8/1994 |
| WO | WO 97/35957 | 10/1997 |
| WO | WO 98/20020 | 5/1998 |
| WO | WO 98/38326 | 9/1998 |
| WO | WO 99/19341 | 4/1999 |
| WO | WO 99/25724 | 5/1999 |
| WO | WO 00/49142 | 4/2000 |
| WO | WO 00/29616 | 5/2000 |
| WO | WO 00/46386 | 8/2000 |
| WO | WO 02/04597 | 1/2002 |
| WO | WO 02/081490 | 10/2002 |
| WO | WO 02/095073 | 11/2002 |
| WO | WO 02/101004 | 12/2002 |
| WO | WO 03/033718 | 4/2003 |
| WO | WO 03/060084 | 7/2003 |
| WO | WO 03/064611 | 7/2003 |
| WO | WO 2004/034028 | 4/2004 |
| WO | WO 2005/107939 | 11/2005 |
| WO | WO 2005/123956 | 12/2005 |
| WO | WO 2006/044956 | 4/2006 |
| WO | WO 2006/049843 | 5/2006 |
| WO | WO 2006/127423 | 11/2006 |
| WO | WO 2007/008951 | 1/2007 |
| WO | WO 2007/009082 | 1/2007 |
| WO | WO 2007/075438 | 7/2007 |
| WO | WO 2007/087347 | 8/2007 |
| WO | WO 2007/117396 | 10/2007 |
| WO | WO 2007/123742 | 11/2007 |
| WO | WO 2007/136833 | 11/2007 |
| WO | WO 2007/136835 | 11/2007 |
| WO | WO 2007/136840 | 11/2007 |
| WO | WO 2008/024319 | 2/2008 |
| WO | WO 2008/054543 | 5/2008 |
| WO | WO 2008/076368 | 6/2008 |
| WO | WO 2008/130629 | 10/2008 |

OTHER PUBLICATIONS

Afshari et al. "Application of Complementary DNA Microarray Technology to Carcinogen Identification, Toxicology, and Drug Safety". Cancer Research, 59, 4759-4760, Oct. 1, 1999.

Aihara, H., et al. "A Conformational Switch Controls the DNA Cleavage Activity of a Integrase," Molecular Cell, 12: 187-198, (Jul. 2003).

Akhundova A.A. et al. "RNA synthesis on immobilized DNA templates in vitro." Biochemistry—Moscow, 43(5):626-628 (1978).

Altschul, S., et al. "Basic local alignment search tool," J Mol Biol., 215(3):403-10, (1990).

Altschul, S. & Koonin, E. "Iterated profile searches with PSI-BLAST—a tool for discovery in protein databases," Trends Biochem. Sci., 23:444-447, (1998).

Andersen, J., et al. "New Unstable Variants of Green Fluorescent Protein for Studies of Transient Gene Expression in Bacteria," Applied and Environmental Microbiology, 64(6):2240-2246 (Jun. 1998).

Bartsevich, V., et al. "Engineered Zinc Finger Proteins for Controlling Stem Cell Fate," Stem Cells, 21:632-637 (2003).

Beier M. and Hohseil J.D. "Analysis of DNA-microarray produced by inverse in situ oligonucleotide synthesis." J. Biotechnology, 94:15-22 (2002).

Boltner, D., et al. "R391: A Conjugative Integrating Mosaic Comprised of Phage, Plasmid, and Transposon Elements," J. of Bacteriology, 184(18):5158-5169 (Sep. 2002).

Booth, P.M., et al. "Assembly and cloning of coding sequences for neurotrophic factors directly from genomic DNA using polymerase chain reaction and uracil DNA glycosylase," Gene 146:303-308 (1994).

Brown, Chappell "BioBricks to help reverse-engineer life," URL: http://eetimes.com/news/latest/showArticle.ihtml?articleiD=21700333 (Jun. 11, 2004).

Burge, C. & Karlin, S. "Prediction of complete gene structures in human genomic DNA," J Mol Biol., 268(1):78-94, (1997).

Chakrabarti R. and Schutt C. Novel Sulfoxides facilitate GC-rich template amplification., 2002, BioTechniques 32(4):866-873.

Caruthers et al. CXV. Total synthesis of the structural gene for an alanine transfer RNA from yeast. Enzymic joining to form the total DNA duplex J Mol Biol. Dec. 28, 1972;72(2):475-92.

Carr, P., et al. "Protein-mediated error-correction for de novo DNA synthesis," Nucleic Acids Research, 32(20), e162 (9 pages), (2004).

Cassell, G. & Segall, A. "Mechanism of Inhibition of Site-specific Recombination by the Holliday Junction-trapping Peptide WKHYNY: Insights into Phage I integrase-mediated Strand Exchange," J. Mol. Bioi., 327:413-429, (2003).

Chalmers, F.P., et al. "Scaling Up the Ligase Chain Reaction-Based Approach to Gene Synthesis" BioTechniques 30:249-252 (2001).

Chan, L. et al. "Refactoring bacteriophage T7," Molecular Systems Biol., doi: 10.1038/msb4100025, (Published online Sep. 13, 2005).

Chandrasegaran, S., et al. "Chimeric Restriction Enzymes: What is Next?," Biol. Chern., 380:841-848 (1999).

Chang, C., et al. "Evolution of a cytokine using DNA family shuffling," Nature Biotechnology, 17: 793-797(1999).

Che, A. "BioBricks++: Simplifying Assembly of Standard DNA Components," [Online] XP002412778, URL:http://austinche.name/docs/bbpp.pdf (Jun. 9, 2004).

Chen, H.B., et al. "A new method for the synthesis of a structural gene," Nucleic Acids Research 18(4):871-878 (1990).

Cherepanov A "Joining of short DNA oligonucleotides with base pair mismatches by T4 DNA ligase" J Biochem. Jan. 2001;129(1):61-8.

Chevalier, B., et al. "Design, Activity, and Structure of a Highly Specific Artificial Endonuclease," Molecular Cell, 10:895-905 (2002).

Chevalier, B., et al. "Homing endonucleases: structural and functional insight into the catalysts of intron/intein mobility", Nucl. Acids Res., 29(18):3757-3774 (2001).

Christians, F., et al. "Directed evolution of thymidine kinase for AZT phosphorylation using DNA family shuffling," Nature Biotechnology, 17:259-264(1999).

Crameri, A, et al. "DNA shuffling of a family of genes from diverse species accelerates directed evolution," Nature, 391:288-291(1998).

Crameri, A, et al. "Improved Green Fluorescent Protein by Molecular Evolution Using DNA Shuffling," Nature Biotechnology, vol. 14, Mar. 1996, pp. 315-319.

(56) References Cited

OTHER PUBLICATIONS

Crameri, A, et al. "Molecular evolution of an arsenate detoxification pathway by DNA shuffling," Nature Biotechnology, 15:436-438 (1997).
Coco, W., et al. "Growth Factor Engineering by Degenerate Homoduplex Gene Family Recombination," Nature Biotechnology, 20: 1246-1250, (Dec. 2002).
Cui T. et al. "Sepharose-supported DNA as template for RNA synthesis" J. Biotechnology, 66: 225-228 (1998).
Dafhnis-Calas, F., et al. "Iterative in vivo assembly of large and complex transgenes by combining the activities of <DC31 integrase and Cre recombinase," Nucleic Acids Research, 33(22): 1-14 (2005).
Dedkova, L. et al. "Enhanced D-Amino Acid Incorporation into Protein by modified Ribosomes," J. Am. Chem. Soc., 125:6616-6617, (2003).
Evans, E. & Alani, E. "Roles for Mismatch Repair Factors in Regulating Genetic Recombination," Molecular & Cellular Biology, 20(21):7839-7844 (Nov. 2000).
Ferretti, L. et al. "Total synthesis of a gene for bovine rhodopsin," PNAS, 83:599-603 (Feb. 1986).
Ferrin, L.J., et al. "Sequence-specific ligation of DNA using RecA protein," Proc. Natl. Acad. Sci. USA, 95: 2152-2157 (1998).
Fisch, I. et al. "A Strategy of Exon Shuffling for Making Large Peptide Repertoires Displayed on Filamentous Bacteriophage," Proceedings of the National Academy of Sciences of USA, 93:7761-7766, (Jul. 1996).
Fleck, O. & Nielsen O. "DNA Repair," J. Cell Science, 117:515-517 (2004).
Fujita K. and Silver J. "Surprising liability of biotin-streptavidin bond during transcription of biotinylated DNA bound to paramagnetic streptavidin beads.", BioTechniques, 14:608-617 (1993).
Gao, X. et al. "Thermodynamically balanced inside-out (TBIO) PCR-based gene synthesis: a novel method of primer design for high fidelity assembly of longer gene sequences," Nucleic Acids Research, 31(22):e143 (11 pages) (2003).
Gardner, T., et al. "Construction of a genetic toggle switch in *Escherichia coli*," Nature, 403:339-342 (Jan. 2000).
Gibbs, W. "Synthetic Life," Scientific American, [Online] URL: htto://www.sciam.com/orint_version.cfm?articleiD=0009FCA4, (Apr. 26, 2004).
Goler, J. "BioJADE: A Design and Simulation Tool for Synthetic Biological Systems," MIT Computer Science and Artificial Intelligence Laboratory, AI Technical Report, [Online] URL: http://dspace.mit.edu/bitstream/1721.1/30475/2/MIT-CSAIL-TR-2004-036.pdf,_(May 2004).
Guntas, G., et al. "A molecular switch created by in vitro recombination of nonhomologous genes," Chem. & Biol., 11: 1483-1487 (Nov. 2004).
Guntas, G., et al. "Directed Evolution of Protein Switches and Their Application to the Creation of Ligand-Binding Proteins," Proc. Natl. Acad. Sci. USA, 102(32):11224-11229 (Aug. 9, 2005).
Hacia J.G. "Resequencing and mutational analysis using oligonucleotide microarrays", Nature Genetics, 21(1 suppl):42-47, 1999.
Hacia J.G. et al. "Applications of DNA chips for genomic analysis". Mol Psychiatry. Nov. 1998;3(6):483-92.
Hansen, W. & Kelley M. "Review of Mammalian DNA Repair and Transcriptional Implications," J. Pharmacol. & Exper. Therapeutics, 295(1): 1-9, (2000).
Hecker, K.H., et al. "Error Analysis of chemically Synthesized Polynucleotides," BioTechniques, 24:256-260 (1998).
Heeb, S., et al. "Small, Stable Shuttle Vectors Based on the Minimal pVS1 Replicon for Use in Gram-Negative Plant-Associated Bacteria," MPMI, 13(2):232-237 (2000).
Hermeling, S., et al. "Structure-Immunogenicity Relationships of Therapeutic Proteins," Pharmaceutical Research, 21(6): 897-903, (Jun. 2004).
Ibrahim EC et al. "Serine/arginine-rich protein-dependent suppression of exon skipping by exonic splicing enhancers" Proc Natl Acad Sci US A. Apr. 5, 2005;102(14):4927-8.
Ito R et al. "Novel muteins of human necrosis factor alpha" Biochimica Biophysica Acta (1991), vol. 1096, pp. 245-252.
Jayaraman K. et al. "Polymerase chain reaction-mediated gene synthesis: synthesis of a gene coding for isozyme c of horseradish peroxidase." Proc Natl Acad Sci US A. May 15, 1991; 88(10): 4084-4088.
Johnston M. "Gene chips: Array of hope for understanding gene regulation". Current Biology, 8: (5) R171, 1998.
Jones, T., et al. "The Development of a Modified Human IFN-alpha2b Linked to the Fe Portion of Human IgG1 as a Novel Potential Therapeutic for the Treatment of Hepatitis C Virus Infection," Journal of Interferon & Cytokine Research, 24:560-572, (2004).
Kampke T. "Efficient primer design algorithms" Bioinformatics, 2001, vol. 17, No. 3, pp. 214-225.
Khaitovich, P., et al. "Characterization of functionally active subribosomal particles from *Thermus aquaticus*," Proc. Natl. Acad. Sci., 96:85-90 (1999).
Kim, C., et al. "Biological lithography: Improvements in DNA synthesis methods," J. Vac. Sci. Technol. B 22(6):3163-3167 (2004).
Kim J.H. et al. "Solid-phase genetic engineering with DNA immobilized on a gold surface." J. Biotechnology, 2002, 96:213-22.
Kim, Y., et al. "Insertion and Deletion Mutants of FokI Restriction Endonuclease," J. Biol. Chem., 269(50):31978-31982 (1994).
Kisselev, L., et al. "Termination of translation: interplay of mRNA, rRNAS and release factors?," The EMBO J., 22(2): 175-182, (2003).
Kitamura, K., et al. "Construction of Block-Shuffled Libraries of DNA for Evolutionary Protein Engineering: Y-Ligation-Based Block Shuffling." Protein Engineering, 15(10): 843-853, (Oct. 2002).
Kleppe K., et al. "Studies of polynucleotides: repair replication of short synthetic DNA's as catalyzed by DNA polymerases," J. Mol. Biol. 56:341-361, (1971).
Kolisnychenko, V., et al. "Engineering a Reduced *Escherichia coli* Genome," Genome Research, 12:640-647, (2002).
Kotsopoulou, E., et al. "A Rev-Independent Human Immunodeficiency Virus Type 1 (HIV-1)-Based Vector That Exploits a Codon-Optimized HIV-1 gag-pol Gene," Journal of Virology, 74(10):4839-4852, (May 2000).
Kowalczykowski, S. "Initiation of genetic recombination and recombination-dependent replication," TIBS, 25:156-165, (Apr. 2000).
Kowalczykowski, S. "In vitro reconstitution of homologous recombination reactions," Experientia, 50:204-215, (1994).
Kurian et al. "DNA chip technology". J Pathol. Feb. 1999; 187(3):267-71.
Krieg A "Real-time detection of nucleotide incorporation during complementary DNA strand analysis" Chem. Bio. Chem. 4:589-592 (2003).
Lashkari et al. "An automated multiplex oligonucleotide synthesizer: Development of high throughput, low cost DNA synthesis". 1995, PNAS 92(17): 7912-7915.
Lamers, M., et al. "ATP Increases the Affinity between MutS ATPase Domains," J. Biol. Chem., 279(42):43879-43885, (Oct. 15, 2004).
Lee, K., et al. "Genetic approaches to Studying Protein Synthesis: Effects of Mutations at ΨI516 and A535 in *Escherichia coli* 16S rRNA," J. Nutr., 131:2994S-3004S, (2001).
Lewis, J. & Hatfull, G. "Control of directionality in intergrase-mediated recombination: examination of recombination directionality factors (RDFs) including Xis and Cox proteins," Nucl. Acids Res., 29(11):2205-2216 (2001).
Li, C., and Evans, R. "Ligation independent cloning irrespective of restriction site compatibility," Nucl. Acids Res., 25(20):4165-4166 (1997).
Li L et al. "Alteration of the cleavage distance of Fok I restriction endonuclease by insertion mutagenesis." Proc Natl Acad Sci USA. 90(7): 2764-2768 (Apr. 1993).
Link, A., et al. "Methods for generating precise deletions and insertions in the genome of wild-type *Escherichia coli*: Application to open reading frame characterization," J. Bacteriol., 179(20):6228-6237, (Oct. 1997).
Liu G. et al. "DNA computing on surfaces." Nature, 403:175179 (2000).
Liu, W. et al. "Genetic Incorporation of Unnatural Amino Acids Into Proteins in Mammalian Cells," Nature Methods, 4(3):239-244, (Mar. 2007).

(56) References Cited

OTHER PUBLICATIONS

Luo, P., et al. "Development of a Cytokine Analog with Enhanced Stability Using Computational Ultrahigh Throughput Screening," Protein Science, 11:1218-1226, (2002).

Lutz, S. & Benkovic, J. "Homology-Independent Protein Engineering," Current Opinion in Biotechnology, 11:319-324, (2000).

Mandecki W. "Oligonucleotide-directed double-strand break repair in plasmids of *Escherichia coli*: a method for site-specific mutagnenesis." 1986, PNAS, 83:7177-7181.

Mannervik, B. "Optimizing the Heterologous Expression of Glutathione Transferase," Methods in Enzymology, 401:254-265, (2005).

Mezard, C., et al. "Recombination Between Similar But Not Identical DNA Sequences During Yeast Transformation Occurs Within Short Stretches of Identity," Cell, 70:659-670, (Aug. 21, 1992).

Miick, S., et al. "Crossover isomer bias is the primary sequence-dependent property of immobilized Holliday junctions," Proc. Natl. Acad. Sci. USA, 94:9080-9084, (Aug. 1997).

Milton, R., et al. "Total Chemical Synthesis of a D-Enzyme: The Enantiomers ofHIV-1 Protease Show Demonstration of Reciprocal Chiral Substrate Specificity," Science, 256:1445-1448, (Jun. 5, 1992).

Mitra R.D. et al. "Fluorescent in situ sequencing on polymerase colonies." Analytical Biochemistry, 320: 55-65 (2003).

Modrich, P. "Strand-specific Mismatch Repair in Mammalian Cells," J. Biol. Chem., 272(40): 24727-24730, (Oct. 3, 1997).

Moore, G. & Maranas C. "Computational Challenges in Combinatorial Library Design for Protein Engineering," AIChE Journal, 50(2):262-272, (Feb. 2004).

Morton, Oliver "Life, Reinvented," Wired, http:www.wired.com/wired/archive!13.01/mit_pr.html (2005).

Nakamaye, K., et al. "Direct sequencing of polymerase chain reaction amplified DNA fragments through the incorporation of deoxynucleoside alpha-thiotriphosphates," Nucleic Acids Research, 16(21):9947-9959, (1988).

Nakamura, Y. & Ito, K. "How protein reads the stop codon and terminates translation," Genes to Cells, 3:265-278, (1998).

Ness, J., et al. "DNA shuffling of subgenomic sequences of subtilisin," Nature Biotechnology 17: 893-896 (1999).

Ness, J., et al. "Synthetic Shuffling Expands Functional Protein Diversity by Allowing Amino Acids to Recombine Independently" Nature Biotechnology, 20:1251-1255, (Dec. 2002).

Nilsson, L., et al. "Improved Heterologous Expression of Human Glutathione Transferase A4-4 by Random Silent Mutagenesis of Codons in the 5' Region," Biochemica et Biophysica Acta, 1528: 101-106, (2001).

Nilsson P. et al. "Real-Time monitoring of DNA manipulations using biosensor technology" Analytical Biochemistry, 1995, 224:400-408.

Noirot, P. & Kolodner, R. "DNA Strand Invasion Promoted by *Esherichia coli* RecT Protein," J. Biol. Chern., 273(20):12274-12280, (May 15, 1998).

Novy, R., et al. "Ligation Independent Cloning: Efficient Directional Cloning of PCR Products," Novagen, Inc., InNovations, 5: 1-3, http://www.emdbiosciences.com/html/NVG/inNovations.html), (1996).

Osawa, S., et al. "Recent Evidence for Evolution of the Genetic Code," Microbiological Reviews, 56(1):229-264, (Mar. 1992).

Osborn, A. & Boltner, D. "When phage, plasmids, and transposons collide: genomic islands, and conjugative and mobilizable-transposons as a mosaic continuum," Plasmid, 48:202-212, (2002).

Panet A. and Khorana G.H. "Studies of polynucleotides: the linkage of deoxyribopolynucleotides templates to cellulaose and its use in their replication." J. Biol. Chern. 249(16):5213-5221 (1974).

Parr, R. & Ball, J. "New donor vector for generation of histidine-tagged fusion proteins using the Gateway Cloning System," Plasmid, 49:179-183, (2003).

Peters, J. & Craig, N. "Tn7: Smarter Than We Thought," Nature, 2:806-814, (Nov. 2001).

Posfai, G., et al. "In vivo excision and amplification of large segments of the *Escherichia coli* genome," Nucl. Acids Res., 22(12):2392-2398, (1994).

Posfai, G., et al. "Markerless gene replacement in *Escherichia coli* stimulated by a double-strand break in the chromosome," Nucl. Acids Res., 27(22):4409-4415, (1999).

Regalado, A. "Next Dream for Venter: Create Entire Set of Genes From Scratch," Wall Street Journal, A1, (Jun. 29, 2005).

Reyrat, J., et al. "Counterselectable Markers: Untapped Tools for Bacterial Genetics and Pathogenesis," Infection and Immunity, 66(9):4011-4017, (Sep. 1998).

Rouwendal, G., et al. "Enhanced Expression in Tobacco of the Gene Encoding Green Fluorescent Protein by Modification of its Codon Usage," Plant Molecular Biology, 33:989-999, (1997).

Ryu, D.D.Y., et al. "Recent Progress in Biomolecular Engineering," Biotechnol. Prog. 16: 2-16 (2000).

Sa-Ardyen, P., et al. "The flexibility of DNA double crossover molecules," Biophys. J., 84:3829-3837, (Jun. 2003).

Saiki, R., et al. "Analysis of enzymatically amplified beta-globin and HLA-DQ alpha DNA with allele-specific oligonucleotide probes," Nature, 324(6093):163-166, (Nov. 13, 1986).

Sakabe, N., et al. "A Bioinformatics Analysis of Alternative Exon Usage in Human Genes Coding for Extracellular Matrix Proteins," Genetics and Molecular Research, 3(4):532-544, (2004).

Sakamoto, K., et al. "Site-Specific Incorporation of an Unnatural Amino Acid Into Proteins in Mammalian Cells," Nucleic Acids Research, 30(21):4692-4699, (2002).

Saks, M., et al. "An Engineered Tetrahymena $tRNA^{GLn}$, for in Vivo Incorporation of Unnatural Amino Acids into Proteins by Nonsense Suppression," J. of Biol. Chem., 271(38):23169-23175, (Sep. 20, 1996).

Saks, M. "Making sense out of nonsense," PNAS, 98(5): 2125-2127, (Feb. 27, 2001).

Salyers, A., et al. "Conjugative Transposons: an Unusual and Diverse Set of Integrated Gene Transfer Elements," Microbiological Reviews, 59(4):579-590, (Dec. 1995).

Sato, T., et al. "Production of menaquinone (vitamin K2)-7 by *Bacillus subtilis*," J. of Bioscience and Engineering, 91(1):16-20, (2001).

Semizarov, D., et al. "Stereoisomers of Deoxynucleoside 5'-Triphosphates as Substrates for Template- dependent and -independent DNA Polymerases," J. Biol. Chem., 272(14)9556-9560 (1997).

Sgaramella, V., et al. "Studies of polynucleotides, C.: A novel joining reaction catalyzed by T4-polynucleotide ligase", PNAS, 67(3): 1468-1475, (Nov. 1970).

Shao, Z., et al. "Random-Priming In Vitro Recombination: An Effective Tool for Directed Evolution," Nucleic Acids Research, 26(2):681-683, (1998).

Sieber, V., et al. "Libraries of Hybrid Proteins From Distantly Related Sequences," Nature Biotechnology, 19: 456-460, (May 2001).

Simon, D., et al. "N-methyl-D-aspartate receptor antagonists disrupt the formation of a mammalian neural map" Proc Natl Acad Sci USA, 89: 10593-10597, (Nov. 1992).

Smith, H.O., et al. "Generating a synthetic genome by whole genome assembly:<DX174 bacteriophage from synthetic oligonucleotides," PNAS, 100(26):15440-15445 (2003).

Smith, J., et al. "A detailed study of the substrate specificity of a chimeric restriction enzyme." Nucleic Acids Research 27(2):674-681 (1999).

Smith, J. & Modrich, P. "Mutation Detection with MutH, MutL, and MutS Mismatch Repair Proteins," Proc. Natl. Acad. Sci. USA, 93:4374-4379, (Apr. 1996).

Soderlind et al. "Domain libraries: Synthetic diversity for de novo design of antibody V-regions." Gene, 160 (1995) 269-272.

Sprinzl, M. & Vassilenko, K. "Compilation of tRNA sequences and sequences of tRNA genes," Nucleic Acids Research, 33:D139-D140 (2005).

Stamm et al., "Sanchored PCR: PCR with CDNA Coupled to a solid phase," Nucleic Acids Research, 19(6):1350, (Mar. 25, 1991).

Steuer, Shawn et al. "Chimeras of the Homing Endonuclease Pi-Scel and the Homologous *Candida tropicalis* Intein a Study to Explore the Possibility of Exchanging DNA-Binding Modules to Obtain Highly Specific Endonucleases With Altered Specificity" ChemBioChem, vol. 5 Issue 2, pp. 206-213, (2004).

(56) References Cited

OTHER PUBLICATIONS

Strizhov et al. "A synthetic cryiC gene, encoding a *Bacillus thuringiensis* delta-endotoxin, confers *Spodotera* resistance in Alfafa and Tobacco" P.N.AS., 1996, vol. 93, No. 26, pp. 15012-15017.
Tan, S., et al. "Zinc-finger protein-targeted gene regulation: Genomewide single-gene specificity," PNAS, 100(21):11997-12002, (Oct. 14, 2003).
Tang K. et al. "Chip-based genotyping by mass spectrometry." PNAS, 96:10016-10020 (1999).
Tsutakawa, S. & Morikawa, K. "The Structural Basis of Damaged DNA Recognition and Endonucleolytic Cleavage for Very Short Patch Repair Endonuclease," Nucleic Acids Research, 29(18):3775-3783, (2001).
Urata, H., et al. "Synthesis and properties of mirror-image DNA," 20(13):3325-3332 (1992).
von Neumann T. "The general and logical theory of automata," Pergamon Press, Taub A.H (Editor) vol. 5, 288-326 (1948).
Waters, V. "Conjugation between bacterial and mammalian cells," Nature Genetics, 29:375-376, (Dec. 2001).
Weiler and Hoheisel "Combining the Preparation of Oligonucleotide Arrays and Synthesis of High-Quality Primers." Analytical Biochemistry, vol. 243, Issue 2, Dec. 15, 1996, pp. 218-227.
Wheeler DL "Database resources of the National Center for Biotechnology Information" Nucleic Acids Res. 29(1): 11-6(Jan. 2001).
Wilgenbus & Lichter "DNA chip technology ante portas" J. Mol. Med 1999, 77:761-768.
Xie, J. & Schultz, P. "An Expanding Genetic Code," Methods a Companion to Methods in Enzymology, 36:227-238, (2005).
Xiong, A., et al. "A simple, rapid, high-fidelity and cost-effective PCR-based two-step DNA synthesis method for long gene sequences," Nucleic Acids Research, 32(12):e98 (10 pages), (2004).
Xu, Y. & Kool, E. "A novel5'-iodonucleoside allows efficient nonenzymatic ligation of single-stranded and duplex DNAs," Tetrahedron Letters, 38(32):5595-5598, (1997).
Xuei et al. "Use of SAM(2)(R) biotin capture membrane in microarrayed compound screening (mu ARCS) format for nucleic acid polymerization assays" Journal of Biomolecular Screening 8:273-282 (2003).
Yolov et al."RNA—synthesis by use of T7-RNA-Polymerase and immobilized DNA in a flowing-type reactor". Bioorganicheskaya Khimiya, 17:789-794 (1991).
Yoon, Y., et al. "Cre/IoxP-mediated in vivo excision of large segments from yeast genome and their amplification based on the 2 um plasmid-derived system," Gene, 223:67-76, (1998).
Yoon, Y. & Koob, M. "Efficient cloning and engineering of entire mitochondrial genomes in *Escherichia coli* and transfer into transcriptionally active mitochondria," Nucleic Acids Research, 31(5):1407-1415, (2003).
Zha, D., et al. "Assembly of Designed Oligonucleotides as an Efficient Method for Gene Recombination: A New Tool in Directed Evolution," ChemBioChem, 4: 34-39, (2003).
Zhang, P. et al. "Rational Design of a Chimeric Endonuclease Targeted to Notl Recognition Site" Protein Engineering Design & Selection, 20(10):497-504, (Oct. 2007).
Zhang, Z., et al. "Selective Incorporation of 5-Hydroxytryptophan Into Proteins in Mammalian Cells," Proceedings of The National Academy of Sciences of The United States of America, 101(24):8882-8887, (Jun. 15, 2004).
Zhao, H., et al. "Molecular Evolution by Staggered Extension Process (Step) In Vitro Recombination," Nature Biotechnology, 16:258-261, (Mar. 1998).
Zhou. X., et al. "Microfluidic PicoArray synthesis of oligodeoxynucleotides and simultaneous assembling of multiple DNA sequences," Nucleic Acids Research, 32(18):5409-5417 (2004).
Extended European Search Report based on European Application No. 10013056 dated Apr. 21, 2011.
Copy Form SB/08 communicated to the Office during prosecution of U.S. Appl. No. 10/243,367 stamped Feb. 22, 2006.
Copy Form SB/08 communicated to the Office during prosecution of U.S. Appl. No. 10/243,367 stamped Mar. 3, 2008.
Copy Form SB/08 communicated to the Office during prosecution of U.S. Appl. No. 10/243,367 stamped Mar. 20, 2006.
Copy Form SB/08 communicated to the Office during prosecution of U.S. Appl. No. 10/243,367 stamped Jun. 26, 2006.
Copy Form SB/08 communicated to the Office during prosecution of U.S. Appl. No. 10/243,367 stamped Aug. 30, 2007.
Copy Form SB/08 communicated to the Office during prosecution of U.S. Appl. No. 12/488,662 stamped Apr. 20, 2010.
Copy Form SB/08 communicated to the Office during prosecution of U.S. Appl. No. 12/488,662 stamped Oct. 27, 2010.
Wiedmann, M., "Ligase chain reaction (LCR)—overview and applications", 3:S51-S64, http://genome.cshlp.org/content/3/4/S51.refs.html, Copyright 1994 by Cold Spring Harbor Laboratory.
COPY Canadian Office for Application No. 2,498,746 dated Jan. 15, 2015.

* cited by examiner

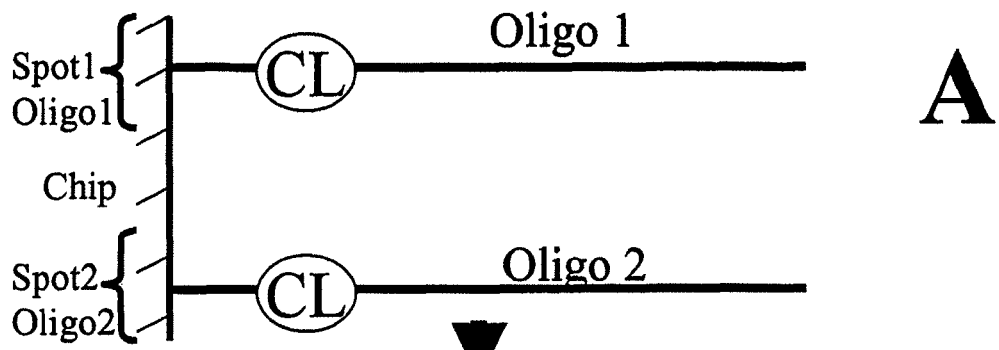
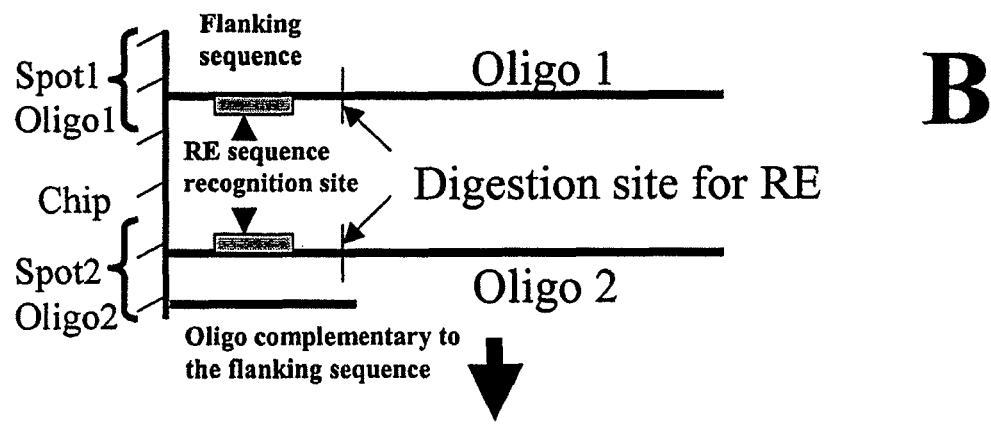
Figure 3

Cleavable linker for oligonucleotide synthesis

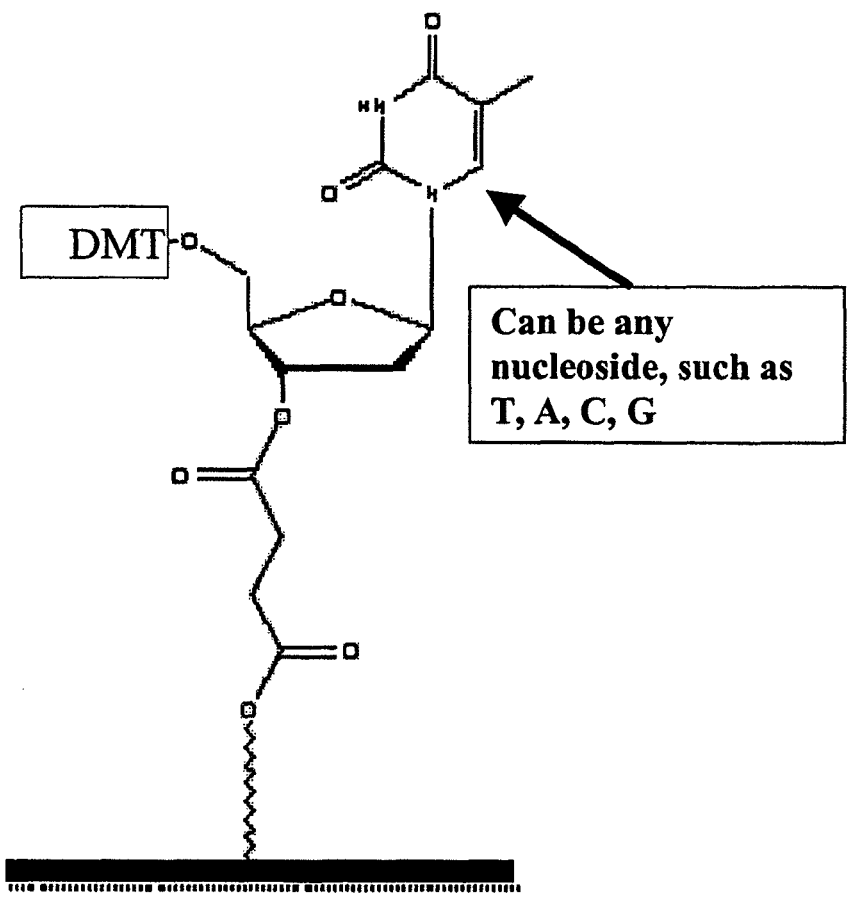

Shown is 5'-dimetoxytrityl-thymidine-3'succinate
Can be other nucleosides, such as A, G, C
T = 5'-dimetoxytrityl-thymidine-3'succinate
dC = 4-N-benzoyl-5'-dimethoxytrityl-deoxycytidine-3'-succinate,
dA = 1-N-benzoyl-5'-dimethoxytrityl-deoxyadenosine-3'-succinate,
dG = 2-N-isobutyryl-5'-dimethoxytrityl-deoxyguanosone-3'-succinate

Figure 3 C

1
Chip-          Primer X
3'<u>TAATTATGCTGAgTGATATCCCTTTC</u>TACCTGTGCGGCTGGCGGACGACGA
AGTCGAATGTGGAGGGCCGTCTAAGGTGTCT5' (82mer)

2
Chip-                              HpaII-site
3'GGACGACGAAGTCGAATGTGGAG*GGCC*GTCTAAGGTGTCTTAAAGTAT
CGACTGATGAAACTCTGCTCGTCGGTCACGAGGTTC-5' (84mer)

3
CHIP-
3'GTATCGACTGATGAAACTCTGCTCGTCGGTCACGAGGTTCCCTCGACCA
CCGCAT<u>GATGTTTCTGCTACTGCTGTTCACGATTATC</u>-5' (86mer)
                          Primer Z Final product: 172mer (one of two strands is shown, direction is 3' to 5' for convenience)

3'<u>TAATTATGCTGAgTGATATCCCTTTC</u>TACCTGTGCGGCTGGCGGACGACGA

AGTCGAATGTGGAG*GGCC*GTCTAAGGTGTCTTAAAGTATCGACTGATGA

AACTCTGCTCGTCGGTCACGAGGTTCCCTCGACCACCGCAT<u>GATGTTTCTG</u>

<u>CTACTGCTGTTCACGATTATC</u>5'

Figure 5

1: CCATCACGCTGAGTCTTACGTACGTAATACGACTCACTATAGGGAAAGTCGCCACCATGGACACGCCGACGAGAGACGACTCCTAATCGAA

2: CCATCACGCTGAGTCTTACGCGCCTGCTGCTTCAGCTACACCTCCCGGCAGATTCCACAGAATTTCGAGACGACTCCTAATCGAA

3: CCATCACGCTGAGTCTTACGATAGCTGACTACTTTGAGACGAGCAGCCAGTGCTCCAAGCCGGTGTCGAGACGACTCCTAATCGAA

4: CCATCACGCTGAGTCTTACGATCTTCCTAACCAAGCGAAGCCGGCAGGTCTGTGCGACCCGAGACGACTCCTAATCGAA

5: CCATCACGCTGAGTCTTACGCAGGCACTCAGCTCTACGGGGCCGTCGCCGATGGGGTGTTCTGCTGGTAGTGGTCGGCGAGCTGCATATT
TCTGGACCCACTCCTCACTGAGACGACTCCTAATCGAAC

6: CCATCACGCTGAGTCTTACGATATTTCTGGACCCACTCCTCACTGGGGTCAGCACAGACCTGCCGAGACGACTCCTAATCGAA

7: CCATCACGCTGAGTCTTACGGGCTTCGCTTGGTTAGGAAGATGACACCGGGCTTGGAGCACTGGCGAGACGACTCCTAATCGAA

8: CCATCACGCTGAGTCTTACGTGCTCCGTCTCAAAGTAGTCAGCTATGAAATTCTGCCGAGACGACTCCTAATCGAA

9: CCATCACGCTGAGTCTTACGGGGAGGTGTAGCTGAAGCAGCAGGGGTCGCCGTGTCCATGGTGGGGACGAGAGACGACTCCTAATCGAA

Figure 8

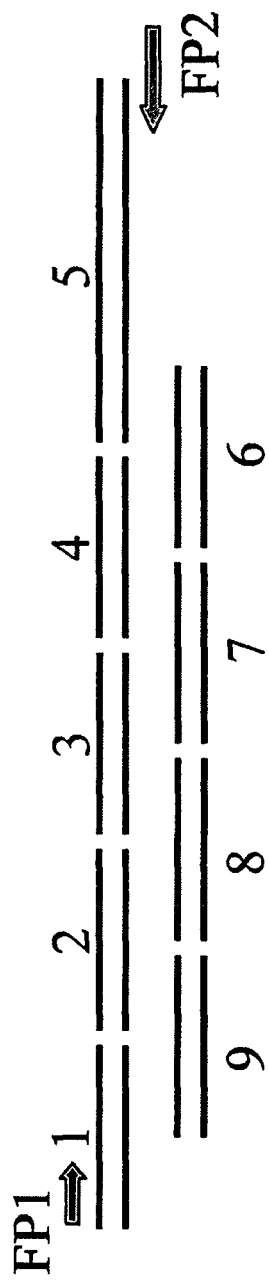
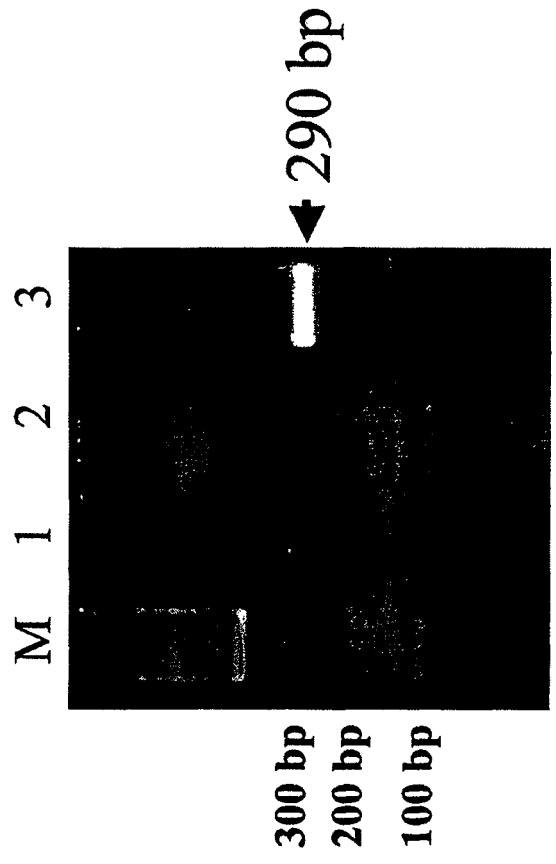
Figure 9

1: TACGTAATACGACTCACTATAGGGAAAGTCGCCACCATGGACACGCCGAC

2: CGCCTGCTGCTTCAGCTACACCTCCCGGCAGATTCCACAGAATTTC

3: ATAGCTGACTACTTTGAGACGAGCAGCCAGTGCTCCAAGCCCGGTGTC

4: ATCTTCCTAACCAAGCGAAGCCGGCAGGTCTGTGCTGACCCC

5: AGTGAGGAGTGGGTCCAGAAATATGTCAGCGACCTAGAGCTGAGTGC

6: ATATTTCTGGACCCACTCCTCACTGGGGTCAGCACAGACCTGCC

7: GGCTTCGCTTGGTTAGGAAGATGACACCGGGCTTGGAGCACTGGC

8: TGCTCGTCTCAAAGTAGTCAGCTATGAAATTCTGTGGAATCTGCC

9: GGGAGGTGTAGCTGAAGCAGCAGGCGGTCGGCGTGTCCATGGTGGCGAC

1F: GGTGAACAGCTCCTCGCCCTTGCTCACCATGGCACTCAGCTCTAGGTCGCTGAC

2F: CATGGTGAGCAAGGGCGAGGAGCTGTTCACCGGGGTGGTGCCCATCCTGGTC

3F: TTGTGGCCGTTTACGTCGCCGTCCAGCTCGACCAGGATGGGCACCACCCC

4F: GAGCTGGACGGCGACGTAAACGGCCACAAGTTCAGCGTGTCCGGCGAGGGC

5F: TTGCCGTAGGTGGCATCGCCCTCGCCCTCGCCGGACACGCTGAAC

6F: GAGGGCGATGCCACCTACGGCAAGCTGACCCTGAAGTTCATCTGCACC

7F: CAGGGCACGGGCAGCTTGCCGGTGGTGCAGATGAACTTCAGGGTCAGC

8F: ACCGGCAAGCTGCCCGTGCCCTGGCCCACCCTCGTGACCACCCTGACCTACGGC

9F: GGGGTAGCGGCTGAAGCACTGCACGCCGTAGGTCAGGGTGGTCACGAGGGTGGGC

10F: GTGCAGTGCTTCAGCCGCTACCCCGACCACATGAAGCAGCACGACTTC

11F: GTAGCCTTCGGGCATGGCGGACTTGAAGAAGTCGTGCTGCTTCATGTGGTC

12F: TTCAAGTCCGCCATGCCCGAAGGCTACGTCCAGGAGCGCACCATCTTCTTC

13F: GGGTCTTGTAGTTGCCGTCGTCCTTGAAGAAGATGGTGCGCTCCTGGAC

Figure 10 (continued)

```
14F: AAGGACGACGGCAACTACAAGACCCGCGCCGAGGTGAAGTTCGAGGGC
15F: AGCTCGATGCGGTTCACCAGGGTGTCGCCCTCGAACTTCACCTCGGCGC
16F: GACACCCTGGTGAACCGCATCGAGCTGAAGGGCATCGACTTCAAGGAGGAC
17F: TCCAGCTTGTGCCCCAGGATGTTGCCGTCCTCCTTGAAGTCGATGCCCTTC
18F: GGCAACATCCTGGGGCACAAGCTGGAGTACAACTACAACAGCCACAACGTC
19F: GTTCTTCTGCTTGTCGGCCATGATATAGACGTTGTGGCTGTTGTAGTTGTAC
20F: TATATCATGGCCGACAAGCAGAAGAACGGCATCAAGGTGAACTTCAAGATC
21F: ACGCTGCCGTCCTCGATGTTGTGGCGGATCTTGAAGTTCACCTTGATGCC
22F: CGCCACAACATCGAGGACGGCAGCGTGCAGCTCGCCGACCACTACCAGC
23F: ACGGGGCCGTCGCCGATGGGGGTGTTCTGCTGGTAGTGGTCGGCGAGCTGC
24F: AGAACACCCCATCGGCGACGGCCCCGTGCTGCTGCCCGACAACCACTACC
25F: TTTGCTCAGGGCGGACTGGGTGCTCAGGTAGTGGTTGTCGGGCAGCAGC
26F: TGAGCACCCAGTCCGCCCTGAGCAAAGACCCCAACGAGAAGCGCGATCAC
27F: GGCGGTCACGAACTCCAGCAGGACCATGTGATCGCGCTTCTCGTTGGGGTC
28F: ATGGTCCTGCTGGAGTTCGTGACCGCCGCCGGGATCACTCTCGGCATGGAC
29F: GGCGGCCGCTTTACTTGTACAGCTCGTCCATGCCGAGAGTGATCCCGGC
```

Figure 10
(continuation)

MICROARRAY SYNTHESIS AND ASSEMBLY OF GENE-LENGTH POLYNUCLEOTIDES

CROSS-REFERENCE TO RELATED APPLICATIONS

This application is a continuation of U.S. patent application Ser. No. 12/488,662, filed on Jun. 22, 2009, which is a continuation of U.S. patent application Ser. No. 10/243,367, filed on Sep. 12, 2002, the content of all of which is incorporated herein by reference in their entirety.

TECHNICAL FIELD OF THE INVENTION

The present invention provides a process for in vitro synthesis and assembly of long, gene-length polynucleotides based upon assembly of multiple shorter oligonucleotides synthesized in situ on a microarray platform. Specifically, the present invention provides a process for in situ synthesis of oligonucleotide sequence fragments on a solid phase microarray platform and subsequent, "on chip" assembly of larger polynucleotides composed of a plurality of smaller oligonucleotide sequence fragments.

BACKGROUND OF THE INVENTION

In the world of microarrays, biological molecules (e.g., oligonucleotides, polypeptides and the like) are placed onto surfaces at defined locations for potential binding with target samples of nucleotides or receptors. Microarrays are miniaturized arrays of biomolecules available or being developed on a variety of platforms. Much of the initial focus for these microarrays have been in genomics with an emphasis of single nucleotide polymorphisms (SNPs) and genomic DNA detection/validation, functional genomics and proteomics (Wilgenbus and Lichter, *J. Mol. Med.* 77:761, 1999; Ashfari et al., *Cancer Res.* 59:4759, 1999; Kurian et al., *J. Pathol.* 187:267, 1999; Hacia, *Nature Genetics* 21 suppl.: 42, 1999; Hacia et al., *Mol. Psychiatry* 3:483, 1998; and Johnson, *Curr. Biol.* 26:R171, 1998).

There are, in general, three categories of microarrays (also called "biochips" and "DNA Arrays" and "Gene Chips" but this descriptive name has been attempted to be a trademark) having oligonucleotide content. Most often, the oligonucleotide microarrays have a solid surface, usually silicon-based and most often a glass microscopic slide. Oligonucleotide microarrays are often made by different techniques, including (1) "spotting" by depositing single nucleotides for in situ synthesis or completed oligonucleotides by physical means (ink jet printing and the like), (2) photolithographic techniques for in situ oligonucleotide synthesis (see, for example, Fodor U.S. patent '934 and the additional patents that claim priority from this priority document, (3) electrochemical in situ synthesis based upon pH based removal of blocking chemical functional groups (see, for example, Montgomery U.S. Pat. No. 6,092,302 the disclosure of which is incorporated by reference herein and Southern U.S. Pat. No. 5,667,667), and (4) electric field attraction/repulsion of fully-formed oligonucleotides (see, for example, Hollis et al., U.S. Pat. No. 5,653,939 and its duplicate Heller U.S. Pat. No. 5,929,208). Only the first three basic techniques can form oligonucleotides in situ e.g., building each oligonucleotide, nucleotide-by-nucleotide, on the microarray surface without placing or attracting fully formed oligonucleotides.

With regard to placing fully formed oligonucleotides at specific locations, various micro-spotting techniques using computer-controlled plotters or even ink-jet printers have been developed to spot oligonucleotides at defined locations. One technique loads glass fibers having multiple capillaries drilled through them with different oligonucleotides loaded into each capillary tube. Microarray chips, often simply glass microscope slides, are then stamped out much like a rubber stamp on each sheet of paper of glass slide. It is also possible to use "spotting" techniques to build oligonucleotides in situ. Essentially, this involves "spotting" relevant single nucleotides at the exact location or region on a slide (preferably a glass slide) where a particular sequence of oligonucleotide is to be built. Therefore, irrespective of whether or not fully formed oligonucleotides or single nucleotides are added for in situ synthesis, spotting techniques involve the precise placement of materials at specific sites or regions using automated techniques.

Another technique involves a photolithography process involving photomasks to build oligonucleotides in situ, base-by-base, by providing a series of precise photomasks coordinated with single nucleotide bases having light-cleavable blocking groups. This technique is described in Fodor et al., U.S. Pat. No. 5,445,934 and its various progeny patents. Essentially, this technique provides for "solid-phase chemistry, photolabile protecting groups, and photolithography . . . to achieve light-directed spatially-addressable parallel chemical synthesis."

The electrochemistry platform (Montgomery U.S. Pat. No. 6,092,302, the disclosure of which is incorporated by reference herein) provides a microarray based upon a semiconductor chip platform having a plurality of microelectrodes. This chip design uses Complimentary Metal Oxide Semiconductor (CMOS) technology to create high-density arrays of microelectrodes with parallel addressing for selecting and controlling individual microelectrodes within the array. The electrodes turned on with current flow generate electrochemical reagents (particularly acidic protons) to alter the pH in a small "virtual flask" region or volume adjacent to the electrode. The microarray is coated with a porous matrix for a reaction layer material. Thickness and porosity of the material is carefully controlled and biomolecules are synthesized within volumes of the porous matrix whose pH has been altered through controlled diffusion of protons generated electrochemically and whose diffusion is limited by diffusion coefficients and the buffering capacities of solutions. However, in order to function properly, the microarray biochips using electrochemistry means for in situ synthesis has to alternate anodes and cathodes in the array in order to generated needed protons (acids) at the anodes so that the protons and other acidic electrochemically generated acidic reagents will cause an acid pH shift and remove a blocking group from a growing oligomer.

Gene Assembly

The preparation of arbitrary polynucleotide sequences is useful in a "postgenomic" era because it provides any desirable gene oligonucleotide or its fragment, or even whole genome material of plasmids, phages and viruses. Such polynucleotides are long, such as in excess of 1000 bases in length. In vitro synthesis of oligonucleotides (given even the best yield conditions of phosphoramidite chemistry) would not be feasible because each base addition reaction is less than 100% yield. Therefore, researchers desiring to obtain long polynucleotides of gene length or longer had to turn to nature or gene isolation techniques to obtain polynucleotides of such length. For the purposes of this patent application, the term "polynucleotide" shall be used to refer to nucleic acids (either single stranded or double stranded) that are sufficiently long so as to be practically not feasible to make in vitro through single base addition. In view of the exponential drop-off in yields from nucleic acid synthesis chemistries, such as phosphoramidite chemistry, such polynucleotides generally have greater than 100 bases and often greater than 200 bases in length. It should be noted that many commercially useful gene cDNA's often have lengths in excess of 1000 bases.

Moreover, the term "oligonucleotides" or shorter term "oligos" shall be used to refer to shorter length single stranded or double stranded nucleic acids capable of in vitro synthesis and generally shorter than 150 bases in length. While it is theoretically possible to synthesize polynucleotides through single base addition, the yield losses make it a practical impossibility beyond 150 bases and certainly longer than 250 bases.

However, knowledge of the precise structure of the genetic material is often not sufficient to obtain this material from natural sources. Mature cDNA, which is a copy of an mRNA molecule, can be obtained if the starting material contains the desired mRNA. However, it is not always known if the particular mRNA is present in a sample or the amount of the mRNA might be too low to obtain the corresponding cDNA without significant difficulties. Also, different levels of homology or splice variants may interfere with obtaining one particular species of mRNA. On the other hand many genomic materials might be not appropriate to prepare mature gene (cDNA) due to exon-intron structure of genes in many different genomes.

In addition, there is a need in the art for polynucleotides not existing in nature to improve genomic research performance. In general, the ability to obtain a polynucleotide of any desired sequence just knowing the primary structure, for a reasonable price, in a short period of time, will significantly move forward several fields of biomedical research and clinical practice.

Assembly of long arbitrary polynucleotides from oligonucleotides synthesized by organic synthesis and individually purified has other problems. The assembly can be performed using PCR or ligation methods. The synthesis and purification of many different oligonucleotides by conventional methods (even using multi-channel synthesizers) are laborious and expensive procedures. The current price of assembled polynucleotide on the market is about $12-25 per base pair, which can be considerable for assembling larger polynucleotides. Very often the amount of conventionally synthesized oligonucleotides would be excessive. This also contributes to the cost of the final product.

Therefore, there is a need in the art to provide cost-effective polynucleotides by procedures that are not as cumbersome and labor-intensive as present methods to be able to provide polynucleotides at costs below $1 per base or 1-20 times less than current methods. The present invention was made to address this need.

SUMMARY OF THE INVENTION

The present invention provides a process for the assembly of oligonucleotides synthesized on microarrays into a polynucleotide sequence. The desired target polynucleotide sequence is dissected into pieces of overlapping oligonucleotides. In the first embodiment these oligonucleotides are synthesized in situ, in parallel on a microarray chip in a non-cleavable form. A primer extension process assembles the target polynucleotides. The primer extension process uses starting primers that are specific for the appropriate sequences. The last step is PCR amplification of the final polynucleotide product. Preferably, the polynucleotide product is a cDNA suitable for transcription purposes and further comprising a promoter sequence for transcription.

The present invention provides a process for assembling a polynucleotide from a plurality of oligonucleotides comprising:

(a) synthesizing or spotting a plurality of oligonucleotide sequences on a microarray device or bead device having a solid or porous surface, wherein a first oligonucleotide is oligo 1 and a second oligonucleotide is oligo 2 and so on, wherein the plurality of oligonucleotide sequences are attached to the solid or porous surface, and wherein the first oligonucleotide sequence has an overlapping sequence region of from about 10 to about 50 bases that is the same or substantially the same as a region of a second oligonucleotide sequence, and wherein the second oligonucleotide sequence has an overlapping region with a third oligonucleotide sequence and so on;

(b) forming complementary oligo 1 by extending primer 1, wherein primer 1 is complementary to oligo 1;

(c) disassociating complementary oligo 1 from oligo 1 and annealing complementary oligo 1 to both oligo 1 and to the overlapping region of oligo 2, wherein the annealing of complementary oligo 1 to oligo 2 serves as a primer for extension for forming complementary oligo 1+2;

(d) repeating the primer extension cycles of step (c) until a full-length polynucleotide is produced; and (e) amplifying the assembled complementary full length polynucleotide to produce a full length polynucleotide in desired quantities.

Preferably, the solid or porous surface is in the form of a microarray device. Most preferably, the microarray device is a semiconductor device having a plurality of electrodes for synthesizing oligonucleotides in situ using electrochemical means to couple and decouple nucleotide bases. Preferably, the primer extension reaction is conducted through a sequential process of melting, annealing and then extension. Most preferably, the primer extension reaction is conducted in a PCR amplification device using the microarray having the plurality of oligonucleotides bound thereto.

The present invention further provides a process for assembling a polynucleotide from a plurality of oligonucleotides comprising:

(a) synthesizing in situ or spotting a plurality of oligonucleotide sequences on a microarray device or bead device each having a solid or porous surface, wherein the plurality of oligonucleotide sequences are attached to the solid or porous surface, and wherein each oligonucleotide sequence has an overlapping region corresponding to a next oligonucleotide sequence within the sequence and further comprises two flanking sequences, one at the 3' end and the other at the 5' end of each oligonucleotide, wherein each flanking sequence is from about 7 to about 50 bases and comprising a primer region and a sequence segment having a restriction enzyme cleavable site;

(b) amplifying each oligonucleotide using the primer regions of the flanking sequence to form double stranded (ds) oligonucleotides;

(c) cleaving the oligonucleotide sequences at the restriction enzyme cleavable site; and (d) assembling the cleaved oligonucleotide sequences through the overlapping regions to form a full length polynucleotide.

Preferably, the flanking sequence is from about 10 to about 20 bases in length. Preferably, the restriction enzyme cleavable site is a class II endonuclease restriction site sequence capable of being cleaved by its corresponding class II restriction endonuclease enzyme. Most preferably, the restriction endonuclease class II site corresponds to restriction sites for a restriction endonuclease class II enzyme selected from the group consisting of Mly I, BspM I, Bae I, BsaX I, Bsr I, Bmr I, Btr I, Bts I, Fok I, and combinations thereof. Preferably, the flanking sequence further comprises a binding moiety used to purify cleaved oligonucleotides from flanking sequences. Preferably, the process further comprises the step of labeling the flanking sequence during the amplification step (b) using primer sequences labeled with binding moieties. Most preferably, a binding moiety is a small molecule able to be captured, such as biotin captured by avidin or streptavidin, or fluorescein able to be captured by an anti-fluorescein antibody.

The present invention further provides a process for assembling a polynucleotide from a plurality of oligonucleotides comprising:

(a) synthesizing in situ or spotting a plurality of oligonucleotide sequences on a microarray device or bead device each having a solid or porous surface, wherein the plurality of oligonucleotide sequences are attached to the solid or porous surface, and wherein each oligonucleotide sequence has an overlapping region corresponding to a next oligonucleotide sequence within the sequence, and further comprises a sequence segment having a cleavable linker moiety;

(b) cleaving the oligonucleotide sequences at the cleavable linker site to cleave each oligonucleotide complex from the microarray or bead solid surface to form a soluble mixture of oligonucleotides, each having an overlapping sequence; and (c) assembling the oligonucleotide sequences through the overlapping regions to form a full length polynucleotide.

Preferably, the cleavable linker is a chemical composition having a succinate moiety bound to a nucleotide moiety such that cleavage produces a 3'hydroxy nucleotide. Most preferably, the cleavable linker is selected from the group consisting of 5'-dimethoxytrityl-thymidine-3'succinate, 4-N-benzoyl-5'-dimethoxytrityl-deoxycytidine-3'-succinate, 1-N-benzoyl-5'-dimethoxytrityl-deoxyadenosine-3'-succinate, 2-N-isobutyryl-5'-dimethoxytrityl-deoxyguanosone-3'-succinate, and combinations thereof.

The present invention further provides a process for assembling a polynucleotide from a plurality of oligonucleotides comprising:

(a) synthesizing in situ or spotting a plurality of oligonucleotide sequences on a microarray device or bead device each having a solid or porous surface, wherein the plurality of oligonucleotide sequences are attached to the solid or porous surface, and wherein each oligonucleotide sequence has a flanking region at an end attached to the solid or porous surface, and a specific region designed by dissecting the polynucleotide sequence into a plurality of overlapping oligonucleotides, wherein a first overlapping sequence on a first oligonucleotide corresponds to a second overlapping sequence of a second oligonucleotide, and wherein the flanking sequence comprises a sequence segment having a restriction endonuclease (RE) recognition sequence capable of being cleaved by a corresponding RE enzyme;

(b) hybridizing an oligonucleotide sequence complementary to the flanking region to form a double stranded sequence capable of interacting with the corresponding RE enzyme;

(c) digesting the plurality of oligonucleotides to cleave them from the microarray device or beads into a solution; and (d) assembling the oligonucleotide mixture through the overlapping regions to form a full length polynucleotide.

Preferably, the flanking sequence is from about 10 to about 20 bases in length. Preferably, the restriction enzyme cleavable site is a class II endonuclease restriction site sequence capable of being cleaved by its corresponding class II restriction endonuclease enzyme. Most preferably, the restriction endonuclease class II site corresponds to restriction sites for a restriction endonuclease class II enzyme selected from the group consisting of Mly I, BspM I, Bae I, BsaX I, Bsr I, Bmr I, Btr I, Bts I, Fok I, and combinations thereof. Preferably, the process further comprises a final step of amplifying the polynucleotide sequence using primers located at both ends of the polynucleotide.

The present invention further provides a process for creating a mixture of oligonucleotide sequences in solution comprising:

(a) synthesizing in situ or spotting a plurality of oligonucleotide sequences on a microarray device or bead device each having a solid or porous surface, wherein the plurality of oligonucleotide sequences are attached to the solid or porous surface, and wherein each oligonucleotide sequence further comprises two flanking sequences, one at the 3' end and the other at the 5' end of each oligonucleotide, wherein each flanking sequence is from about 7 to about 50 bases and comprising a primer region and a sequence segment having a restriction enzyme cleavable site;

(b) amplifying each oligonucleotide using the primer regions of the flanking sequence to form a double stranded (ds) oligonucleotides; and (c) cleaving the double stranded oligonucleotide sequences at the restriction enzyme cleavable site.

Preferably, the flanking sequence is from about 10 to about 20 bases in length. Preferably, the restriction enzyme cleavable site is a class II endonuclease restriction site sequence capable of being cleaved by its corresponding class II restriction endonuclease enzyme. Most preferably, the restriction endonuclease class II site corresponds to restriction sites for a restriction endonuclease class II enzyme selected from the group consisting of Mly I, BspM I, Bae I, BsaX I, Bsr I, Bmr I, Btr I, Bts I, Fok I, and combinations thereof. Preferably, the flanking sequence further comprises a binding moiety used to purify cleaved oligonucleotides from flanking sequences. Preferably, the process further comprises the step of labeling the flanking sequence during the amplification step (b) using primer sequences labeled with binding moieties. Most preferably, a binding moiety is a small molecule able to be captured, such as biotin captured by avidin or streptavidin, or fluorescein able to be captured by an anti-fluorescein antibody.

The present invention further provides a process for creating a mixture of oligonucleotide sequences in solution comprising:

(a) synthesizing in situ or spotting a plurality of oligonucleotide sequences on a microarray device or bead device each having a solid or porous surface, wherein the plurality of oligonucleotide sequences are attached to the solid or porous surface, and wherein each oligonucleotide sequence has a sequence segment having a cleavable linker moiety;

(b) cleaving the oligonucleotide sequences at the cleavable linker site to cleave each oligonucleotide sequence from the microarray or bead solid surface to form a soluble mixture of oligonucleotides.

Preferably, the cleavable linker is a chemical composition having a succinate moiety bound to a nucleotide moiety such that cleavage produces a 3'hydroxy nucleotide. Most preferably, the cleavable linker is selected from the group consisting of 5'-dimethoxytrityl-thymidine-3'succinate, 4-N-benzoyl-5'-dimethoxytrityl-deoxycytidine-3'-succinate, 1-N-benzoyl-5'-dimethoxytrityl-deoxyadenosine-3'-succinate, 2-N-isobutyryl-5'-dimethoxytrityl-deoxyguanosone-3'-succinate, and combinations thereof.

The present invention further provides a process for creating a mixture of oligonucleotide sequences in solution comprising:

(a) synthesizing in situ or spotting a plurality of oligonucleotide sequences on a microarray device or bead device each having a solid or porous surface, wherein the plurality of oligonucleotide sequences are attached to the solid or porous surface, and wherein each oligonucleotide sequence has a flanking region at an end attached to the solid or porous surface, and a specific region, wherein the flanking sequence comprises a sequence segment having a restriction endonuclease (RE) recognition sequence capable of being cleaved by a corresponding RE enzyme;

(b) hybridizing an oligonucleotide sequence complementary to the flanking region to form a double stranded sequence capable of interacting with the corresponding RE enzyme;

(c) digesting the plurality of oligonucleotides to cleave them from the microarray device or beads into a solution.

Preferably, the flanking sequence is from about 10 to about 20 bases in length. Preferably, the restriction enzyme cleavable site is a class II endonuclease restriction site sequence capable of being cleaved by its corresponding class II restriction endonuclease enzyme. Most preferably, the restriction endonuclease class II site corresponds to restriction sites for a restriction endonuclease class II enzyme selected from the group consisting of Mly I, BspM I, Bae I, BsaX I, Bsr I, Bmr I, Btr I, Bts I, Fok I, and combinations thereof.

BRIEF DESCRIPTION OF THE DRAWINGS

FIG. 1 shows a schematic of gene assembly on a microarray device surface or porous matrix. FIG. 1A also shows, relative to the target sequence, primer Pr1; extension product of primer Pr1, which is complementary to oligonucleotide 1; and extension product of complementary oligonucleotide 1, which is complementary to oligonucleotides 1+2.

FIG. 3 shows a schematic for gene assembly using oligos synthesized and then cleaved from a microarray device. Specifically, in the upper panel marked "A", oligonucleotide sequences are connected to the microarray device through a cleavable linker (CL) moiety. An example of a cleavable linker moiety is provided in FIG. 3A. The cleavable linkers are molecules that can withstand the oligonucleotide synthesis process (i.e., phosphoramidite chemistry) and then can be cleaved to release oligonucleotide fragments. Chemical cleavage at cleavable linker CL recreates usual 3' end of specific oligos 1 through N. These oligonucleotides are released into a mixture. The mixture of oligonucleotides is subsequently assembled into full-length polynucleotide molecules. In the lower panel marked "B" of FIG. 3, oligonucleotide sequences are connected to the microarray device through additional flanking sequence containing a restriction enzyme (RE) sequence site. Another oligonucleotide sequence, complementary to the flanking sequence region, is hybridized to the oligonucleotides on the microarray device. This recreates a "ds" or double-stranded oligonucleotide structure, each having a RE sequence recognition region in the flanking sequence region. Digestion of this ds oligonucleotides with the corresponding RE enzymes at the RE recognition sites in the flanking sequence regions releases the specific oligonucleotides 1 through N. When assembled, oligonucleotide sequences 1 through N form a full-length polynucleotide molecule. FIG. 3C: Cleavable linker for oligonucleotide synthesis.

FIG. 5 shows the oligonucleotide sequences (SEQ ID No 1, SEQ ID NO 2, SEQ ID NO 3) used to assemble the 172-mer polynucleotide (SEQ ID NO 4) of FIG. 4. The sequences of primers X and Z are underlined. The Hpa II restriction site is indicated by italic underlined letters.

FIG. 8 shows the sequences from nine oligonucleotides fragments (consecutively numbered 1-9 and having SEQ ID NO 5, SEQ ID NO 6, SEQ ID NO 7, SEQ ID NO 8, SEQ ID NO 9, SEQ ID NO 10, SEQ ID NO 11, SEQ ID NO 12, and SEQ ID NO 13, respectively) used to assemble a 290 by polynucleotide. The flanking regions are shown in bold and underlined. The process used for polynucleotide assembly was the second embodiment. The overlapping regions further contained a cleavable site as the Mly I recognition site for the Mly I class II restriction endonuclease.

FIG. 9 shows a schematic in the top panel for assembling a polynucleotide from nine oligonucleotides. Nine oligonucleotide sequences, shown in FIG. 8, were amplified by PCR using primers 1 and 2 (as described in FIG. 6) into ds DNA fragments containing the same flanking regions and specific overlapping sequences, digested with Mly I enzyme to remove flanking sequences, and used for assembly of 290 bp DNA fragment. The columns in the gel shown are M—markers, 1—negative control, assembly without primers FP1 and FP2, 2—negative control, assembly without specific oligos, 3—assembly of 290 bp fragment from specific oligos plus amplification with FP1 and FP2 primers. The band in column 3 shows a high efficiency of the inventive polynucleotide assembly process.

FIG. 10 shows a sequence of an assembled polynucleotide in Example 4, broken down into its component oligonucleotides (Fragment 1, SEQ ID NO 14, Fragment 2, SEQ ID NO 15, Fragment 3, SEQ ID NO 16, Fragment 4, SEQ ID NO 17, Fragment 5, SEQ ID NO 18, Fragment 6, SEQ ID NO 19, Fragment 7, SEQ ID NO 20, Fragment 8, SEQ ID NO 21, Fragment 9, SEQ ID NO 22, Fragment 1F, SEQ ID NO 23, Fragment 2F, SEQ ID NO 24, Fragment 3F, SEQ ID NO 25, Fragment 4F, SEQ ID NO 26, Fragment 5F, SEQ ID NO 27, Fragment 6F, SEQ ID NO 28, Fragment 7F, SEQ ID NO 29 Fragment 8F, SEQ ID NO 30, Fragment 9F, SEQ ID NO 31, Fragment 10F, SEQ ID NO 32 Fragment 11F, SEQ ID NO 33, Fragment 12F, SEQ ID NO 34, Fragment 13F, SEQ ID NO 35, Fragment 14F, SEQ ID NO 36, Fragment 15F, SEQ ID NO 37, Fragment 16F, SEQ ID NO 38, Fragment 17F, SEQ ID NO 39, Fragment 18F, SEQ ID NO 40 Fragment 19F, SEQ ID NO 41, Fragment 20F, SEQ ID NO 42, Fragment 21F, SEQ ID NO 43, Fragment 22F, SEQ ID NO 44, Fragment 23F, SEQ ID NO 45, Fragment 24F, SEQ ID NO 46, Fragment 25F, SEQ ID NO 47, Fragment 26F, SEQ ID NO 48, Fragment 27F, SEQ ID NO 49, Fragment 28F, SEQ ID NO 50, Fragment 29F, SEQ ID NO 51).

DETAILED DESCRIPTION OF THE INVENTION

Figure 1A:
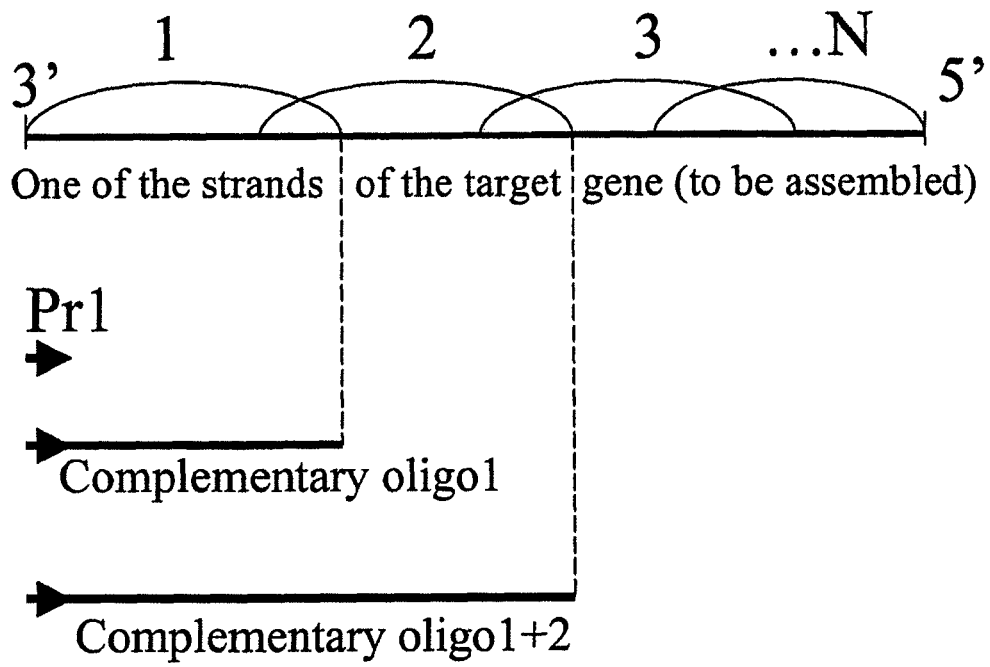
In FIG. 1A, the target gene sequence is dissected into number of overlapping oligonucleotides. The 3' and 5' are the ends of the shown strand.

The present invention describes the preparation of a polynucleotide sequence (also called "gene") using assembly of overlapping shorter oligonucleotides synthesized or spotted on microarray devices or on solid surface bead devices. The shorter oligonucleotides include sequence regions having overlapping regions to assist in assembly into the sequence of the desired polynucleotide. Overlapping regions refer to sequence regions at either a 3' end or a 5' end of a first oligonucleotide sequence that is the same as part of the second oligonucleotide and has the same direction (relative to 3' to 5' or 5' to 3' direction), and will hybridize to the 5' end or 3' end of a second oligonucleotide sequence or its complementary sequence (second embodiment), and a second oligonucleotide sequence to a third oligonucleotide sequence, and so on. In order to design or develop a microarray device or bead device to be used for polynucleotide assembly, the polynucleotide sequence is divided (or dissected) into a number of overlapping oligonucleotides segments, each with lengths preferably from 20 to 1000 bases, and most preferably from 20 to 200 bases (FIG. 1A). The overlap between oligonucleotide segments is 5 or more bases, preferably 15-25 bases to that proper hybridization of first to second, second to third, third to fourth and so on occurs. These oligonucleotides (or oligos) are preferably synthesized on a microarray device using any available method (i.e., electrochemical in situ synthesis, photolithography in situ synthesis, ink jet printing, spotting, etc.). The direction of synthesis relative to the microarray device surface or porous matrix covering a microarray device can be from 3' to 5' or from 5' to 3'. Preferably, in situ synthesis is done in the 3' to 5' direction.

In the first embodiment the inventive gene/polynucleotide assembly process uses oligonucleotides immobilized on a microarray device. The microarray device itself or a porous reaction layer with immobilized oligonucleotides can be used for the inventive gene/polynucleotide assembly process.

Figure 1B:
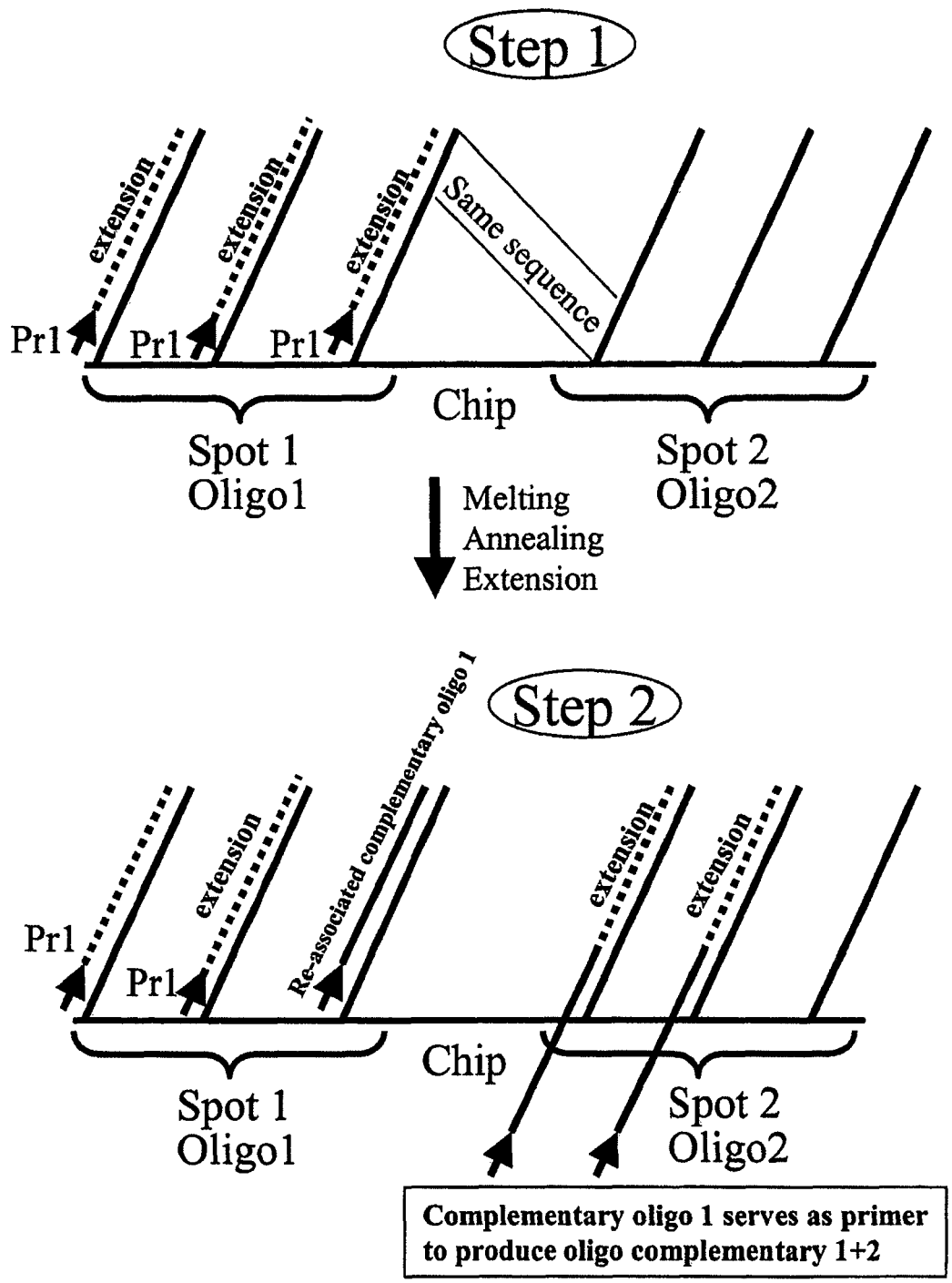
FIG. 1B illustrates one embodiment of the initial steps of an assembly process. In step 1 of assembly, Primer Pr1 is annealed to oligonucleotide 1 and extended by appropriate polymerase enzyme into product complementary to oligonucleotide 1. The second step is melting, re-annealing and extension (i.e., amplification) to lead to production of larger amount of Pr1 extension product (complementary oligonucleotide 1), re-association of the complementary oligonucleotide 1 with oligonucleotide 1, and to annealing of the complementary oligonucleotide 1 with oligonucleotide 2 followed by its extension into product complementary to oligonucleotides 1+2.

With regard to FIG. 1B, the process comprises several repeated steps of melting, annealing and extension (FIG. 1B), which can be performed in any thermal cycler instrument. The cycling program is similar to the programs used for PCR. At the first step of gene/polynucleotide assembly, primer Pr1 is added and anneals to oligonucleotide 1 on the microarray device and then extends by appropriate polymerase enzyme into product complementary to oligonucleotide 1 (called complementary oligonucleotide 1). At the second step of the process the product complementary to oligonucleotide 1 is melted from oligonucleotide 1, primer Pr1 is annealed again to the oligonucleotide 1 as well as product complementary to oligonucleotide 1 is partially re-anneals to oligonucleotide 1 and partially anneals to oligonucleotide 2 due to an overlapping sequence region between oligonucleotide 1 and oligonucleotide 2. Extension of Pr1 leads to production of an additional amount of Pr1 extension product (complementary oligonucleotide 1). The annealing of the complementary oligonucleotide 1 to oligonucleotide 2 followed by its extension leads to product complementary to oligonucleotides 1+2 (called complementary oligonucleotides 1+2). Similarly, at step 3 of the process melting, re-annealing and extension lead to the same products as at step 2 plus a product complementary to oligonucleotides 1+2+3. These cycles of melting, annealing and extension are repeated until full-length polynucleotide is formed. The number of cycles should be equal or more than the number of oligos on microarray device. After formation, the final target polynucleotide molecule is amplified by a PCR process with two primers complementary to the ends of this molecule to the desirable amounts.

In a second embodiment, a plurality of oligonucleotides that together comprise (with overlapping regions) the target polynucleotide sequence are synthesized on a microarray device (or can be synthesized on beads as a solid substrate), wherein each oligonucleotide sequence further comprises flanking short sequence regions, wherein each flanking sequence region comprises one or a plurality of sequence sites for restriction endonuclease, preferably endonuclease class II (ERII) enzymes. Each oligonucleotide is amplified by PCR using appropriate oligonucleotide primers to the flanking sequence regions to form a preparation of a plurality of oligonucleotides. The preparation of oligonucleotides is treated then with appropriate REII enzyme(s) (specific to the restriction sequences in the flanking sequence regions) to produce flanking fragments and overlapping oligonucleotides that, together comprise the desired polynucleotide sequence. Flanking fragments and PCR primers are removed from the mixture, if desired, by different methods based on size or specific labeling of the PCR primers. The oligonucleotides resembling the desired target polynucleotide then assembled into the final target polynucleotide molecule using repetition of the primer extension method and PCR amplification of the final molecule.

Figure 2:
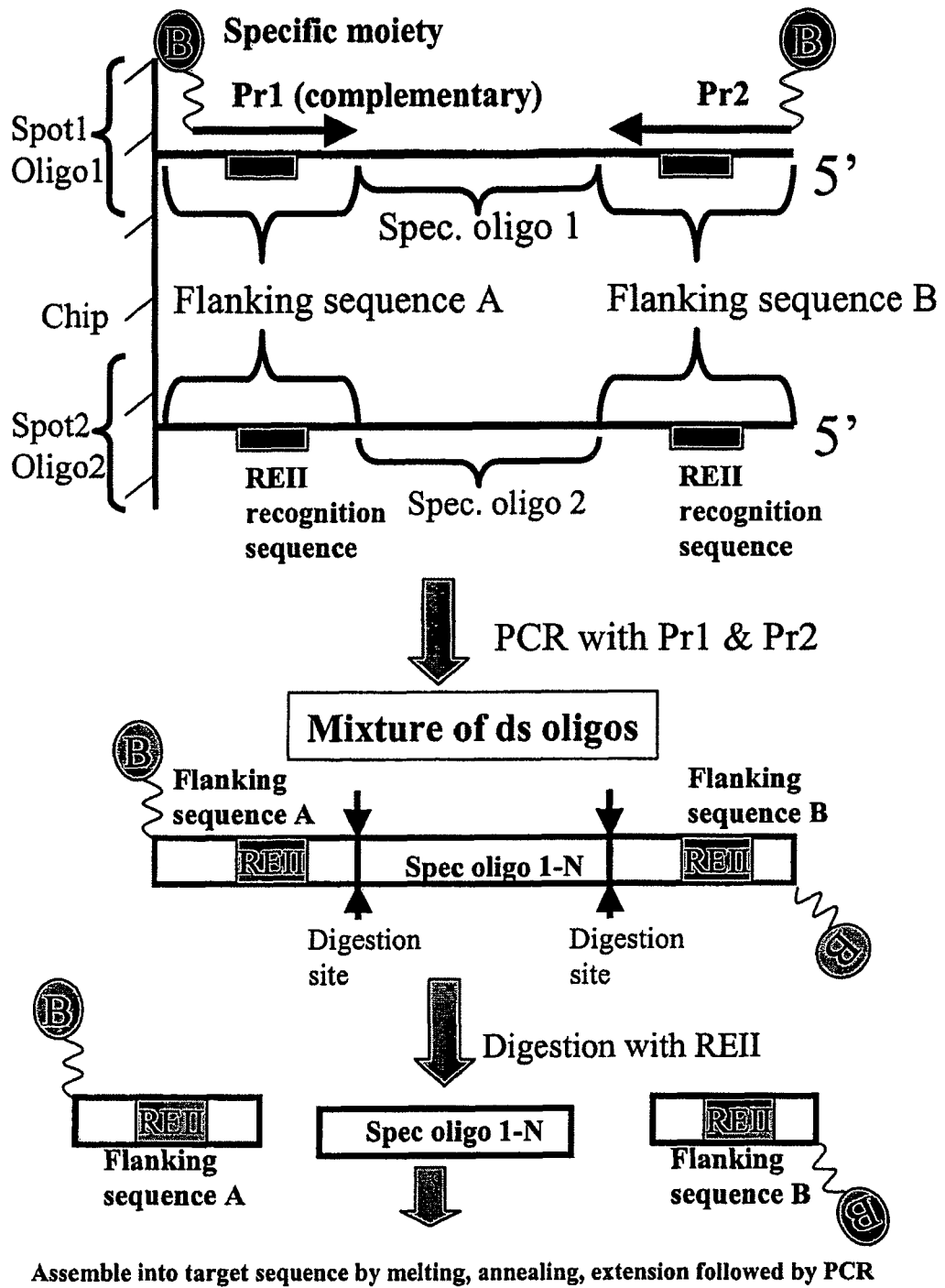
FIG. 2 shows a second embodiment of the inventive gene assembly process using oligonucleotides synthesized in situ onto a microarray device, each having a flanking sequence region containing a restriction enzyme cleavage site, followed by a PCR amplification step and followed by a REII restriction enzyme cleavage step.

Specifically, in the second embodiment, the assembly process initially uses oligonucleotides immobilized on a microarray device or beads, via immobilization techniques, such as spotting or ink jet printing or by direct in situ synthesis of the microarray device using various techniques, such as photolithography or electrochemical synthesis. The overlapping oligonucleotide sequences are designed having an overlapping region and one or two flanking sequence regions comprising a restriction class II recognition site (FIG. 2A). The assembled oligonucleotides together comprise the target polynucleotide sequence.

The length of flanking sequences is at least the length of REII recognition site. The flanking sequences are designed to have minimal homology to the specific oligonucleotide sequences regions on the microarray device. The flanking sequences can be the same for each oligonucleotide fragment, or be two or more different sequences. For example, a pair of appropriate primers, called Pr1 and Pr2, was designed to amplify each oligonucleotide on a microarray device (FIG. 2) by PCR. Each primer may contain a binding moiety, such as biotin, that does not affect their ability to serve as primers. After PCR amplification the amplified ds copy of each oligonucleotide was present in the reaction mixture. This reaction mixture was treated with the appropriate REII enzyme or enzymes specific for the restriction sites in the flanking sequence regions. The digestion sites for REII were designed, after cleavage, to produce the desired specific oligonucleotide sequence fragments that, when assembled will form the target polynucleotide sequence. As a result of digestion a mixture of specific double stranded (ds) overlapping oligonucleotide sequence fragments resembling the structure of desired target polynucleotide, and ds flanking sequences were formed. If desired, these flanking sequences and residual primers are removed from the mixture using specific absorption through specific moieties introduced in the primers (such as, for example, by absorption on avidin beads for biotin-labeled primers), or based on the size difference of the specific oligos and flanking sequences and primers. The mixture of specific oligonucleotide sequences resembling target gene sequence is used to assemble the final target polynucleotide molecule using repeated cycles of melting, self-annealing and polymerase extension followed by PCR amplification of the final target polynucleotide molecule with appropriate PCR primers designed to amplify. This final PCR amplification step is routinely done in the art and described in, for example, Mullis et al., *Cold Spring Harb. Symp. Quant. Biol.* 51 Pt 1:263-73, 1986; and Saiki et al., Science 239:487-91, 1988. PCR amplification steps generally follow manufacturer's instructions. Briefly, A process for amplifying any target nucleic acid sequence contained in a nucleic acid or mixture thereof comprises treating separate complementary strands of the nucleic acid with a molar excess of two oligonucleotide primers and extending the primers with a thermostable enzyme to form complementary primer extension products which act as templates for synthesizing the desired nucleic acid sequence. The amplified sequence can be readily detected. The steps of the reaction can be repeated as often as desired and involve temperature cycling to effect hybridization, promotion of activity of the enzyme, and denaturation of the hybrids formed.

In another embodiment for the assembly step, oligonucleotide sequences that together comprise the target polynucleotide molecule are assembled using a ligase chain reaction as described in Au et al., *Biochem. Biophys. Res. Commun.* 248:200-3, 1998. Briefly, short oligonucleotides are joined through ligase chain reaction (LCR) in high stringency conditions to make "unit fragments" (Fifty microliters of reaction mixture contained 2.2 mM of each oligo, 8 units Pfu DNA ligase (Stratagene La Jolla, Calif.) and reaction buffer provided with the enzyme. LCR was conducted as follows: 95° C. 1 min; 55° C. 1.5 min, 70° C. 1.5 min, 95° C. 30 sec for 15 cycles; 55° C. 2 min; 70° C. 2 min, which are then fused to form a full-length gene sequence by polymerase chain reaction.

In another embodiment the ds oligonucleotide sequences are assembled after preparation by chain ligation cloning as described in Pachuk et al., *Gene* 243:19-25, 2000; and U.S. Pat. No. 6,143,527 (the disclosure of which is incorporated by reference herein). Briefly, chain reaction cloning allows ligation of double-stranded DNA molecules by DNA ligases and bridging oligonucleotides. Double-stranded nucleic acid molecules are denatured into single-stranded molecules. The ends of the molecules are brought together by hybridization to a template. The template ensures that the two single-stranded nucleic acid molecules are aligned correctly. DNA ligase joins the two nucleic acid molecules into a single, larger, composite nucleic acid molecule. The nucleic acid molecules are subsequently denatured so that the composite molecule formed by the ligated nucleic acid molecules and the template cease to hybridize to each. Each composite molecule then serves as a template for orienting unligated, single-stranded nucleic acid molecules. After several cycles, composite nucleic acid molecules are generated from smaller nucleic acid molecules. A number of applications are disclosed for chain reaction cloning including site-specific ligation of DNA fragments generated by restriction enzyme digestion, DNAse digestion, chemical cleavage, enzymatic or chemical synthesis, and PCR amplification.

Figure 1C:
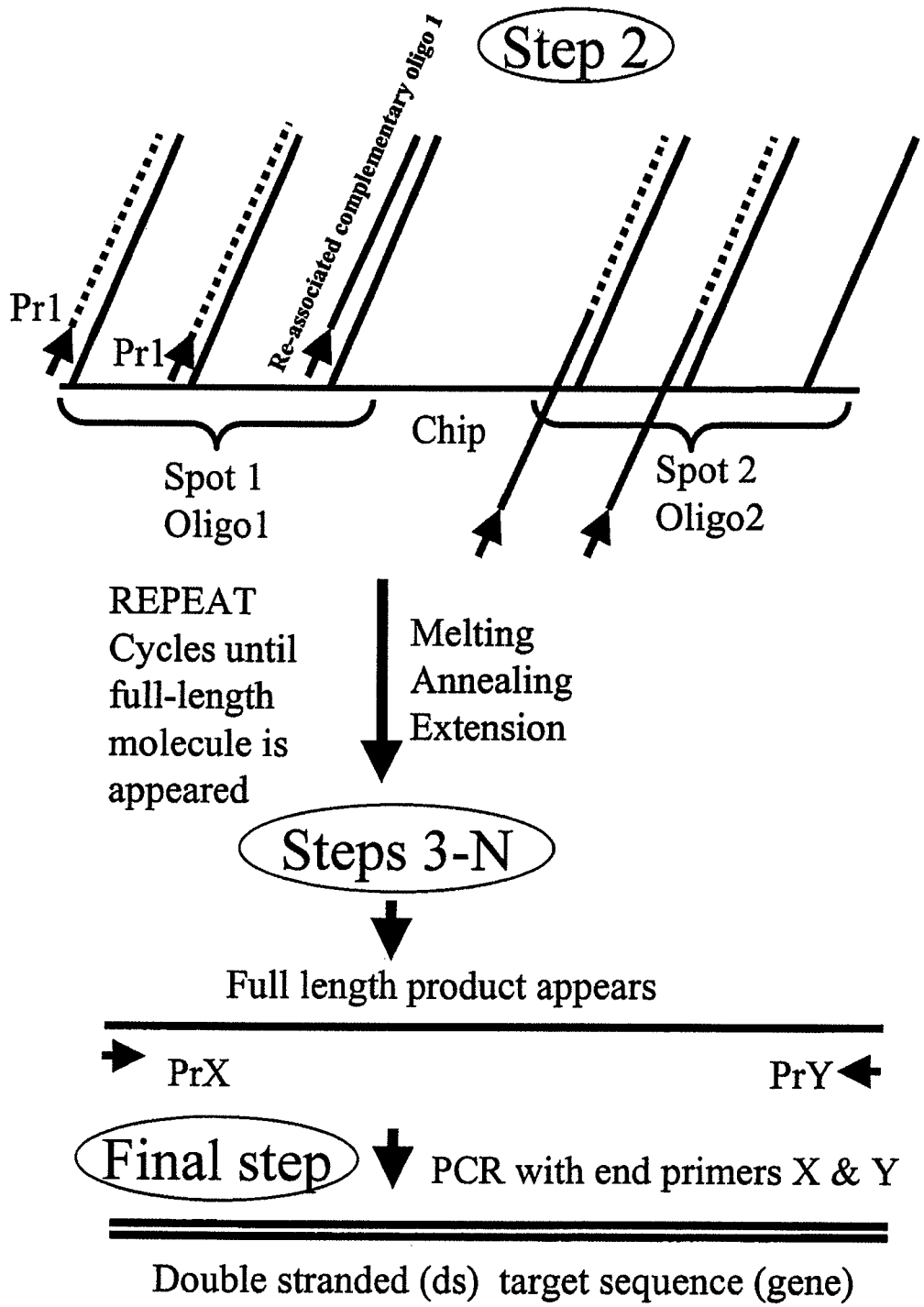
FIG. 1C shows a continuation of the assembly process from FIG. 1B. Specifically, step 3 of the process (i.e., melting, re-annealing and extension) leads to the same products as step 2 plus a product complementary to oligonucleotides 1+2+3. Cycles (steps) are repeated until a full-length complementary polynucleotide is formed. The final step is preparation of the final target polynucleotide molecule in desirable amounts by amplification (i.e., PCR) using two primers complementary to the ends of this molecule (PrX and PrY).

With regard to the second embodiment of the inventive process (illustrated in FIG. 2), a target polynucleotide gene sequence (either strand) is divided into number of overlapping oligonucleotide sequences by hand or with a software program, as shown in FIG. 1. These oligonucleotide sequences, plus flanking sequences A and B (having one or a plurality of restriction enzyme sites in the flanking region sequence), are synthesized (in situ) on microarray device, or on a bead solid surface using standard in situ synthesis techniques, or spotted (pre-synthesized) onto a microarray device using standard oligonucleotide synthesis procedures with standard spotting (e.g., computer-aided or ink jet printing) techniques. The oligonucleotide sequences are amplified, preferably using a PCR process with a pair of primers (Pr1 and Pr2). The primers are optionally labeled with specific binding moieties, such as biotin. The resulting amplified mixture of different amplified oligonucleotide sequences are double stranded (ds). The mixture of ds oligonucleotide sequences are treated with an appropriate restriction enzyme, such as an REII restriction enzyme (e.g., Mly I enzyme), to produce mixture of different double stranded (ds) overlapping oligonucleotide sequences that can be assembled into the structure of the desired polynucleotide (gene) and ds flanking sequences. Optionally, the flanking sequences and residual primers are removed from the ds oligonucleotide sequence mixture, preferably by a process of specific absorption using specific binding moieties introduced in the primers (e.g., biotin), or by a process of size fractionation based on the size differences of the specific oligonucleotide sequences and flanking sequences. The mixture of specific oligonucleotide sequences is assembled, for example, by a process of repeated cycles of melting, self-annealing and polymerase extension followed by PCR amplification of the final molecule with appropriate PCR primers designed to amplify this complete molecule (e.g., as described in Mullis et al., *Cold Spring Harb. Symp. Quant. Biol.* 51 Pt 1:263-73, 1986; and Saiki et al., *Science* 239:487-91, 1988).

In yet another embodiment of the inventive process (illustrated in FIG. 3), the oligonucleotide sequences comprising the target polynucleotide sequence are synthesized on a microarray device or bead solid support, each oligonucleotide having a cleavable linker moiety synthesized within the sequence, such that after synthesis, oligonucleotides can be cleaved from the microarray device into a solution. Examples of appropriate cleavable linker moieties are shown in FIG. 3A. In addition to this method of cleavage, a sequence containing RE enzyme site can be synthesized at the ends of oligonucleotides attached to the microarray device. These oligonucleotides on the microarray device then hybridize with an oligonucleotide complementary to this additional flanking sequence and treated with an RE enzyme specific for the RE enzyme site. This process releases oligonucleotide fragments resembling the structure of the target polynucleotide. This set of oligonucleotides then can be assembled into the final polynucleotide molecule using any one of the methods or combination of the methods of ligation, primer extension and PCR.

In a third embodiment of the inventive process, a plurality of oligonucleotides that can be assembled into a full length polynucleotide are synthesized on a microarray device (or beads having a solid surface) having specific cleavable linker moieties (FIG. 3A) or capable of being cleaved from the solid support of the microarray device or beads by a chemical treatment. The net effect is to recreate the functional 3' ends and 5' ends of each specific oligonucleotide sequence. After treatment to cleave them, the oligonucleotides (each having overlapping regions) are released into a mixture and used for full-length polynucleotide gene assembly using any of the gene assembly processes described herein.

Specifically, in the third embodiment and as illustrated in FIG. 3, a target polynucleotide sequence is dissected into number of overlapping oligonucleotide sequences by a software program or on paper, but not necessarily physically in a laboratory. These oligonucleotide sequences are physically synthesized on a microarray device. In alternative A, the oligonucleotide sequences are connected to the microarray device through cleavable linker moiety. Chemical cleavage under basic conditions (e.g., through addition of ammonia), at cleavable linker CL recreates the usual 3' end of the specific oligonucleotide sequences 1 through N. Oligonucleotide sequences 1 through N are released into a mixture. The mixture of oligonucleotide sequences is used for polynucleotide assembly.

In alternative B, oligonucleotide sequences are connected to a microarray device through additional flanking sequence regions containing a restriction enzyme (RE) sequence site. A second oligonucleotide fragment, complementary to the flanking sequence, is hybridized to the oligonucleotides on the microarray device. This recreates a ds structure at the flanking sequence region, including the RE recognition site. Digestion of this ds DNA structure with RE enzyme specific to the RE recognition site in the flanking sequence region will release specific oligonucleotides 1 through N into a mixture solution. The oligonucleotides 1 through N are able to assemble into a polynucleotide molecule in solution.

In another example of alternative B, oligonucleotides that together assemble into the polynucleotide are synthesized on a microarray device, each having a flanking sequence on the microarray side. The flanking sequence further comprises a restriction endonuclease (RE) recognition site (see FIG. 3B). Oligonucleotides complementary to the flanking sequence region are added and hybridized to the oligonucleotides on microarray device. After hybridization a RE (restriction enzyme specific to the RE sequence in the flanking region) is added to the microarray device. Specific oligonucleotide sequences are released from the microarray device as a result of RE digestion into a mixture. The mixture of specific oligonucleotide sequences ARE assembled into the full-length polynucleotide sequence.

Example 1

Figure 4:
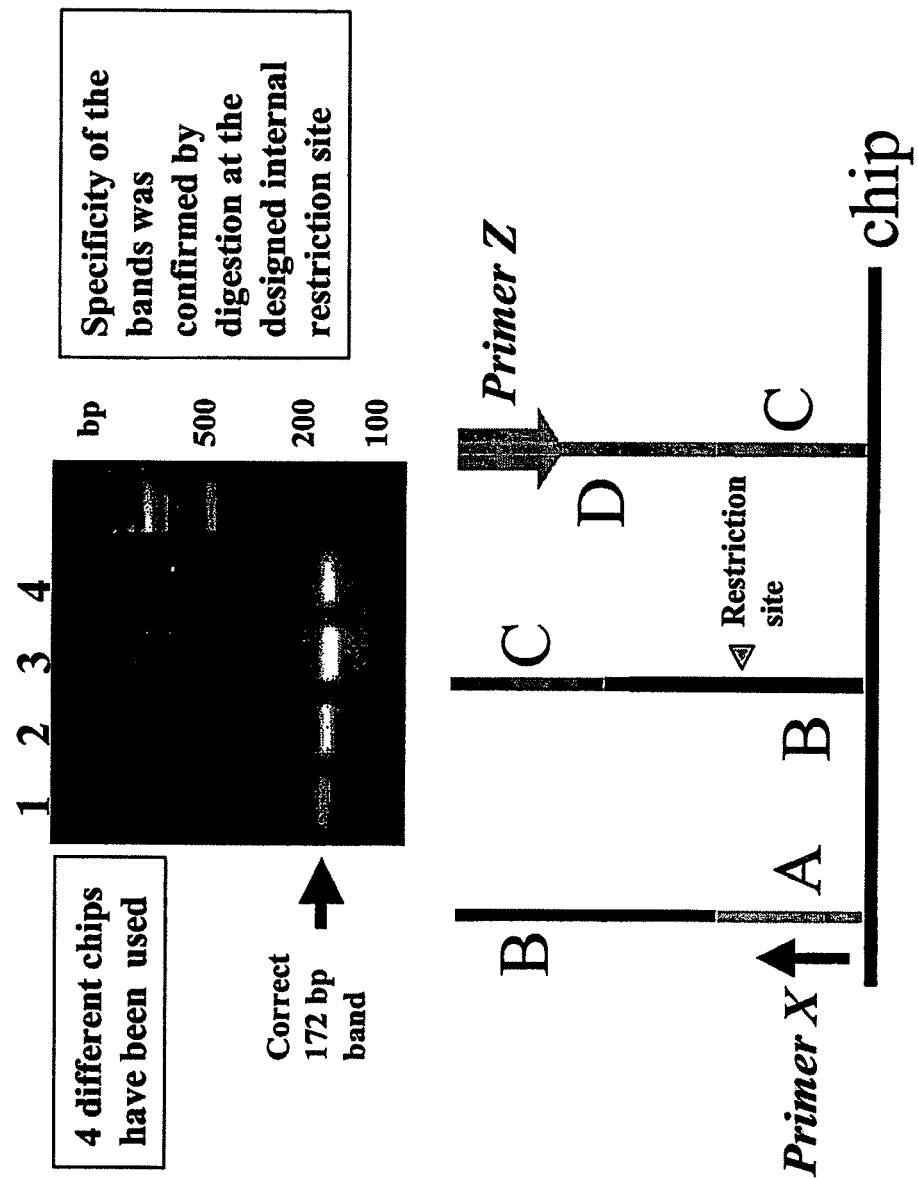
FIG. 4 shows the assembly of a polynucleotide from three oligonucleotide fragments wherein each oligonucleotide fragment was synthesized in situ on a microarray device. The fully assembled polynucleotide was 172 mers in length, a length not practically achievable by in situ synthesis. The first embodiment inventive process was used in this example.

This example illustrates assembly of 172-mer polynucleotide sequence from non-cleavable oligonucleotide sequences synthesized on a microarray device according to the first embodiment inventive process (FIGS. 4 and 5). Three oligonucleotides (sequences shown in FIG. 5) were synthesized in situ on a microarray device according to an electrochemical process (see U.S. Pat. No. 6,093,302, the disclosure of which is incorporated by reference herein). The oligonucleotide sequences synthesized were amplified by a PCR reaction with primers X (complementary to the strand of oligo#1) and Z (same strand as Oligo#3) (FIG. 5). After 45 cycles of PCR using a PCR kit with AmplyGold® enzyme (Applied Biosystems) a correct DNA fragment of 172 bp was synthesized (FIG. 4). Its subsequent digestion confirmed the specificity of this enzyme with Hpa II producing two fragments of 106 bp and 68 bp.

Example 2

This example illustrates the second embodiment of the inventive process for preparing oligonucleotides for assembly into full-length polynucleotides by PCR and REII (restriction enzyme) digestion. A single oligonucleotide sequence was synthesized on a microarray device according to the procedure in Example 1 (see FIGS. 2 and 6). The oligonucleotide sequence further comprised 2 flanking sequences, each having a recognition site for a Mly I restriction enzyme. This microarray device was subject to a PCR (25 cycles) reaction with two primers (shown in FIG. 7) to produce an amplified PCR fragment mixture. The amplified PCR fragment obtained was digested by Mly I restriction enzyme and purified by a PCR purification kit (Qiagen) to produce specific oligonucleotides ready for assembly (FIG. 7). Similarly, this specific oligonucleotide was purified from the flanking sequences by absorption of the digestion mixture by Streptavidin-agarose (Sigma).

Example 3

This example illustrates the assembly of a 290 bp polynucleotide sequence from 9 oligonucleotide sequences, each having flanking sequences containing a MlyI restriction site. Each of the nine different oligonucleotide sequences was synthesized on a microarray device through an in situ electrochemistry process as described in example 1 herein.

Figure 6:
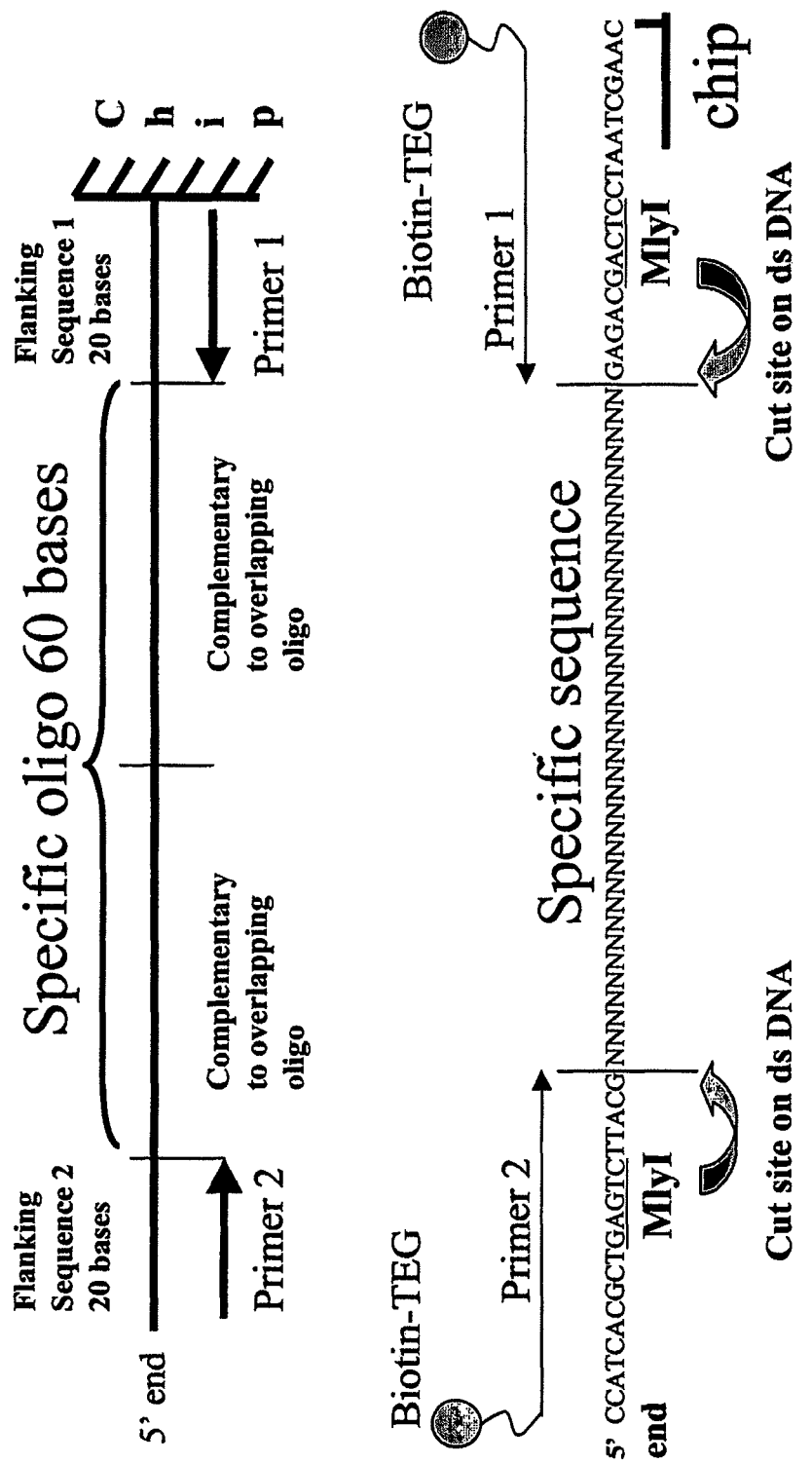
FIG. 6 shows a scheme for preparing the sequences of flanking regions (SEQ ID NO 52 and SEQ ID NO 53) and primers used for preparation of specific oligonucleotide for assembly using the REII enzyme MlyI. Primer 1 is complementary to the oligonucleotide strand on a microarray device and contains a Biotin-TEG (triethylene glycol) moiety. Primer 2 is the same strand as the oligonucleotide strand on microarray device and contains Biotin-TEG moiety. Any sequence between the primers can be used and is just designated by a string of N's.
Figure 7:
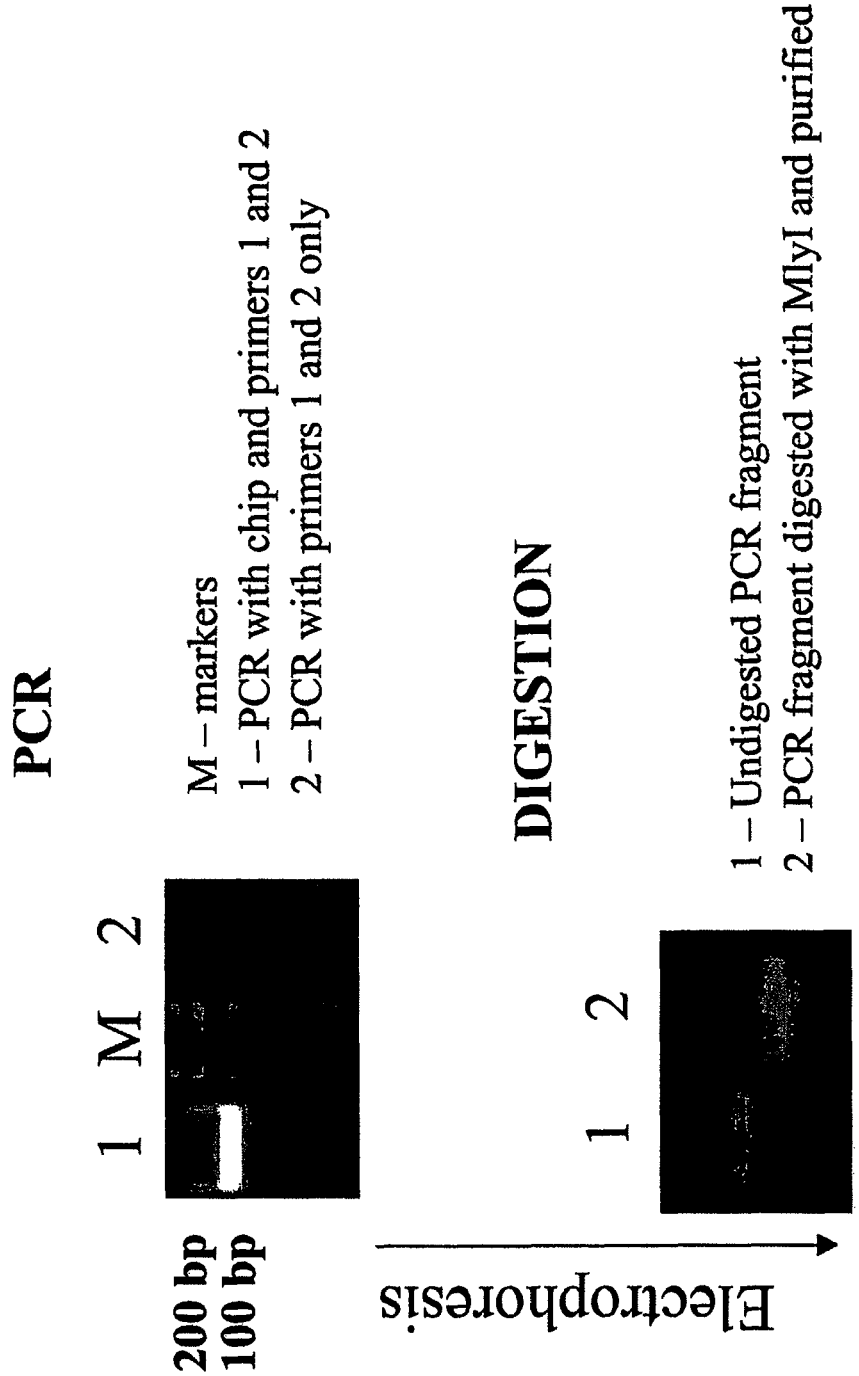
FIG. 7 shows the results of PCR and Mly I digestion of an oligonucleotide sequence as described in FIG. 6. The clean bands show the ability to obtain pure oligonucleotides using the second embodiment of the inventive process to cleave off oligonucleotide sequences using appropriate restriction enzymes.

The microarray device containing the nine specific oligonucleotide sequences (with flanking sequences as shown in FIG. 8) was used for PCR amplification of each oligonucleotide sequence using two primers, Primer 1 and 2, described in FIG. 6 to form a mixture of ds oligonucleotide sequences. The primers were complementary to the flanking sequences. The mixture of the amplified ds oligonucleotide sequences was digested by Mly I enzyme. Specific ds oligonucleotide sequences were purified and then assembled into the final 290 bp polynucleotide sequence in two steps as described in FIG. 2 and shown schematically in FIG. 9. At the first step of assembly 20 cycles of melting-annealing-extension were used. The final product was amplified using two primers FP1 and FP2 (FIG. 9) in 25 cycles of PCR into a 290 bp polynucleotide DNA.

Example 4

This example illustrates the creation of a cDNA polynucleotide sequence capable of coding on expression for fusion protein MIP-GFP-FLAG (Macrophage Inflammation Protein-Green Fluorescence Protein-FLAG peptide) using thirty-eight overlapping oligonucleotide sequences (FIG. 10). The 38 oligonucleotides were synthesized on a microarray device using an electrochemical in situ synthesis approach, as described in example 1. Each oligonucleotide sequence contained a cleavable linker moiety (see FIG. 3A) at their 3' end. After simultaneous deprotection and cleavage of these oligonucleotide sequences by concentrated ammonia, the mixture of oligonucleotide sequences was purified by gel-filtration through the spin column. The purified oligonucleotide sequences were assembled into a polynucleotide by a process shown schematically in FIG. 3. The resulting DNA polynucleotide was 965 bp and contained both a T7 RNA-polymerase promoter and a coding sequence for MIP-GFP-FLAG fusion protein. The polynucleotide assembled in this example was used in a standard transcription/translation reaction and produced the appropriate MIP-GFP-FLAG fusion protein. The translated protein was purified from the reaction mixture using anti-FLAG resin (Sigma). The functional protein possessed green fluorescence signal in appropriate blue light. Accordingly, this experiment demonstrated that the inventive gene assembly process provided the correct DNA sequence coding for the functional protein.

The invention claimed is:

1. A composition for assembly of a target polynucleotide sequence, the composition comprising a plurality of different synthesized oligonucleotide sequences, wherein the plurality of different synthesized oligonucleotide sequences are immobilized on a solid or porous surface, each oligonucleotide sequence comprising a fragment of a target polynucleotide sequence and at least one flanking sequence, wherein the at least one flanking sequence is at the 3' end, or the 5' end, or the 3' end and the 5' end of each fragment, and wherein each flanking sequence comprises a primer binding site and a sequence segment designed to permit removal of the primer binding site such that the fragments together comprise the target polynucleotide sequence.

2. The composition of claim 1 wherein said sequence segment permitting removal of the primer binding site is a class II endonuclease restriction site sequence capable of being cleaved by its corresponding class II restriction endonuclease enzyme.

3. The composition of claim 1 wherein each oligonucleotide comprises a cleavable linker moiety.

4. The composition of claim 1 wherein each oligonucleotide comprises a binding moiety.

5. The composition of claim 1 wherein the flanking sequences are the same.

6. The composition of claim 1 wherein the flanking sequences are designed to have minimal homology to the oligonucleotide fragment sequences.

7. The composition of claim 1 wherein each fragment sequence further comprises an overlapping sequence corresponding to a next oligonucleotide of the composition, and wherein the overlapping sequence is the same as a sequence of a next oligonucleotide, or is complementary to a sequence of the next oligonucleotide.

8. A device comprising a solid or porous surface having a plurality of cleavable oligonucleotide sequences immobilized thereon, wherein each oligonucleotide sequence has an overlapping sequence and at least one flanking sequence,
   wherein the overlapping sequence correspond to a sequence of a next oligonucleotide of the plurality of oligonucleotides, and
   wherein the at least one flanking sequence is at the 3' end, the 5' end, or at the 3' end and 5' end of each overlapping sequence, each flanking sequence comprising a primer binding site and a sequence segment permitting removal of the primer binding site, such that the overlapping sequences together comprise the target polynucleotide sequence.

9. The device of claim 8 wherein each oligonucleotide comprises a cleavable linker moiety.

10. The device of claim 8 wherein the sequence segment comprises a restriction enzyme cleavable site capable of being cleaved by a type II restriction endonuclease.

11. The device of claim 8 wherein the flanking sequence are the same.

12. The device of claim 8 wherein the flanking sequences are designed to have minimal homology to the overlapping sequences.

13. The device of claim 8 wherein each oligonucleotide has an overlapping-sequence that is the same as or complementary to a sequence of the next oligonucleotide.

14. A process for creating a mixture of oligonucleotide sequences in solution, the process comprising:
(a) providing a plurality of oligonucleotide sequences bound on a solid or porous surface, wherein each oligonucleotide sequence comprises a fragment of a target polynucleotide sequence and wherein each oligonucleotide sequence further comprises at least one flanking sequence at the 3' end, the 5' end, or at the 3' end and the 5' end of each fragment, wherein each flanking sequence comprises a primer binding site and a sequence segment having a restriction enzyme site permitting removal of the primer binding site such that the fragments together comprise the target polynucleotide sequence and wherein each oligonucleotide sequence has a cleavable site; and
(b) cleaving the oligonucleotide sequences at the cleavable site to form a soluble mixture of oligonucleotides.

15. The process of claim 14 wherein the restriction enzyme site is a class II endonuclease restriction site sequence capable of being cleaved by its corresponding class II restriction endonuclease enzyme.

16. The process of claim 14 wherein each oligonucleotide comprises a cleavable linker moiety.

17. The process of claim 14 wherein the flanking sequence regions are designed to have minimal homology to the oligonucleotide sequences.

18. The process of claim 14 wherein each oligonucleotide has a sequence region that is the same as or complementary to the sequence region of the next oligonucleotide.

* * * * *

SEQUENCE LISTING

```
<160> NUMBER OF SEQ ID NOS: 53

<210> SEQ ID NO 1
<211> LENGTH: 82
<212> TYPE: DNA
<213> ORGANISM: Artificial Sequence
<220> FEATURE:
<223> OTHER INFORMATION: Synthetic construct

<400> SEQUENCE: 1
taattatgct gagtgatatc cctttctacc tgtgcggctg gcggacgacg aagtcgaatg     60
tggagggccg tctaaggtgt ct                                             82

<210> SEQ ID NO 2
<211> LENGTH: 84
<212> TYPE: DNA
<213> ORGANISM: Artificial Sequence
<220> FEATURE:
<223> OTHER INFORMATION: Synthetic construct

<400> SEQUENCE: 2
ggacgacgaa gtcgaatgtg gagggccgtc taaggtgtct taaagtatcg actgatgaaa     60
ctctgctcgt cggtcacgag gttc                                           84

<210> SEQ ID NO 3
<211> LENGTH: 86
<212> TYPE: DNA
<213> ORGANISM: Artificial Sequence
<220> FEATURE:
<223> OTHER INFORMATION: Synthetic construct

<400> SEQUENCE: 3
gtatcgactg atgaaactct gctcgtcggt cacgaggttc cctcgaccac cgcatgatgt     60
ttctgctact gctgttcacg attatc                                         86

<210> SEQ ID NO 4
<211> LENGTH: 142
<212> TYPE: DNA
<213> ORGANISM: Artificial Sequence
<220> FEATURE:
<223> OTHER INFORMATION: Synthetic construct

<400> SEQUENCE: 4
taattatgct gagtgatatc cctttctacc tgtgcggctg aagtcgaatg tggagggccg     60
tctaaggtgt cttaaagtat aactctgctc gtcggtcacg aggttccctc gaccaccgca   120
gctactgctg ttcacgatta tc                                            142

<210> SEQ ID NO 5
<211> LENGTH: 89
<212> TYPE: DNA
<213> ORGANISM: Artificial Sequence
<220> FEATURE:
<223> OTHER INFORMATION: Synthetic construct
```

```
<400> SEQUENCE: 5
ccatcacgct gagtcttacg tacgtaatac gactcactat agggaaagtc gccaccatgg    60
acacgccgac gagacgactc ctaatcgaa                                      89

<210> SEQ ID NO 6
<211> LENGTH: 85
<212> TYPE: DNA
<213> ORGANISM: Artificial Sequence
<220> FEATURE:
<223> OTHER INFORMATION: Synthetic construct

<400> SEQUENCE: 6
ccatcacgct gagtcttacg cgcctgctgc ttcagctaca cctcccggca gattccacag    60
aatttcgaga cgactcctaa tcgaa                                          85

<210> SEQ ID NO 7
<211> LENGTH: 87
<212> TYPE: DNA
<213> ORGANISM: Artificial Sequence
<220> FEATURE:
<223> OTHER INFORMATION: Synthetic construct

<400> SEQUENCE: 7
ccatcacgct gagtcttacg atagctgact actttgagac gagcagccag tgctccaagc    60
ccggtgtcga gacgactcct aatcgaa                                        87

<210> SEQ ID NO 8
<211> LENGTH: 81
<212> TYPE: DNA
<213> ORGANISM: Artificial Sequence
<220> FEATURE:
<223> OTHER INFORMATION: Synthetic construct

<400> SEQUENCE: 8
ccatcacgct gagtcttacg atcttcctaa ccaagcgaag ccggcaggtc tgtgctgacc    60
ccgagacgac tcctaatcga a                                              81

<210> SEQ ID NO 9
<211> LENGTH: 130
<212> TYPE: DNA
<213> ORGANISM: Artificial Sequence
<220> FEATURE:
<223> OTHER INFORMATION: Synthetic construct

<400> SEQUENCE: 9
ccatcacgct gagtcttacg caggcactca gctctacggg gccgtcgccg atggggtgt     60 tctgctggta gtggtcggcg agctgcatat ttctggaccc actcctcact gagacgactc   120
ctaatcgaac                                                          130

<210> SEQ ID NO 10
<211> LENGTH: 83
<212> TYPE: DNA
<213> ORGANISM: Artificial Sequence
<220> FEATURE:
<223> OTHER INFORMATION: Synthetic construct

<400> SEQUENCE: 10
ccatcacgct gagtcttacg atatttctgg acccactcct cactggggtc agcacagacc    60
tgccgagacg actcctaatc gaa                                            83
```

```
<210> SEQ ID NO 11
<211> LENGTH: 84
<212> TYPE: DNA
<213> ORGANISM: Artificial Sequence
<220> FEATURE:
<223> OTHER INFORMATION: Synthetic construct

<400> SEQUENCE: 11
ccatcacgct gagtcttacg ggcttcgctt ggttaggaag atgacaccgg gcttggagca      60
ctggcgagac gactcctaat cgaa                                            84

<210> SEQ ID NO 12
<211> LENGTH: 84
<212> TYPE: DNA
<213> ORGANISM: Artificial Sequence
<220> FEATURE:
<223> OTHER INFORMATION: Synthetic construct

<400> SEQUENCE: 12
ccatcacgct gagtcttacg tgctcgtctc aaagtagtca gctatgaaat tctgtggaat     60
ctgccgagac gactcctaat cgaa                                           84

<210> SEQ ID NO 13
<211> LENGTH: 88
<212> TYPE: DNA
<213> ORGANISM: Artificial Sequence
<220> FEATURE:
<223> OTHER INFORMATION: Synthetic construct

<400> SEQUENCE: 13
ccatcacgct gagtcttacg gggaggtgta gctgaagcag caggcggtcg gcgtgtccat     60
ggtggcgacg agacgactcc taatcgaa                                       88

<210> SEQ ID NO 14
<211> LENGTH: 50
<212> TYPE: DNA
<213> ORGANISM: Artificial Sequence
<220> FEATURE:
<223> OTHER INFORMATION: Synthetic construct

<400> SEQUENCE: 14
tacgtaatac gactcactat agggaaagtc gccaccatgg acacgccgac                50

<210> SEQ ID NO 15
<211> LENGTH: 46
<212> TYPE: DNA
<213> ORGANISM: Artificial Sequence
<220> FEATURE:
<223> OTHER INFORMATION: Synthetic construct

<400> SEQUENCE: 15
cgcctgctgc ttcagctaca cctcccggca gattccacag aatttc                    46

<210> SEQ ID NO 16
<211> LENGTH: 48
<212> TYPE: DNA
<213> ORGANISM: Artificial Sequence
<220> FEATURE:
<223> OTHER INFORMATION: Synthetic construct

<400> SEQUENCE: 16
atagctgact actttgagac gagcagccag tgctccaagc ccggtgtc                  48

<210> SEQ ID NO 17
```

<210> SEQ ID NO 17
<211> LENGTH: 42
<212> TYPE: DNA
<213> ORGANISM: Artificial Sequence
<220> FEATURE:
<223> OTHER INFORMATION: Synthetic construct

<400> SEQUENCE: 17
atcttcctaa ccaagcgaag ccggcaggtc tgtgctgacc cc          42

<210> SEQ ID NO 18
<211> LENGTH: 47
<212> TYPE: DNA
<213> ORGANISM: Artificial Sequence
<220> FEATURE:
<223> OTHER INFORMATION: Synthetic construct

<400> SEQUENCE: 18
agtgaggagt gggtccagaa atatgtcagc gacctagagc tgagtgc          47

<210> SEQ ID NO 19
<211> LENGTH: 44
<212> TYPE: DNA
<213> ORGANISM: Artificial Sequence
<220> FEATURE:
<223> OTHER INFORMATION: Synthetic construct

<400> SEQUENCE: 19
atatttctgg acccactcct cactggggtc agcacagacc tgcc          44

<210> SEQ ID NO 20
<211> LENGTH: 45
<212> TYPE: DNA
<213> ORGANISM: Artificial Sequence
<220> FEATURE:
<223> OTHER INFORMATION: Synthetic construct

<400> SEQUENCE: 20
ggcttcgctt ggttaggaag atgacaccgg gcttggagca ctggc          45

<210> SEQ ID NO 21
<211> LENGTH: 45
<212> TYPE: DNA
<213> ORGANISM: Artificial Sequence
<220> FEATURE:
<223> OTHER INFORMATION: Synthetic construct

<400> SEQUENCE: 21
tgctcgtctc aaagtagtca gctatgaaat tctgtggaat ctgcc          45

<210> SEQ ID NO 22
<211> LENGTH: 49
<212> TYPE: DNA
<213> ORGANISM: Artificial Sequence
<220> FEATURE:
<223> OTHER INFORMATION: Synthetic construct

<400> SEQUENCE: 22
gggaggtgta gctgaagcag caggcggtcg gcgtgtccat ggtggcgac          49

<210> SEQ ID NO 23
<211> LENGTH: 54
<212> TYPE: DNA
<213> ORGANISM: Artificial Sequence
<220> FEATURE:
<223> OTHER INFORMATION: Synthetic construct

<400> SEQUENCE: 23
ggtgaacagc tcctcgccct tgctcaccat ggcactcagc tctaggtcgc tgac 54

<210> SEQ ID NO 24
<211> LENGTH: 52
<212> TYPE: DNA
<213> ORGANISM: Artificial Sequence
<220> FEATURE:
<223> OTHER INFORMATION: Synthetic construct

<400> SEQUENCE: 24
catggtgagc aagggcgagg agctgttcac cggggtggtg cccatcctgg tc 52

<210> SEQ ID NO 25
<211> LENGTH: 50
<212> TYPE: DNA
<213> ORGANISM: Artificial Sequence
<220> FEATURE:
<223> OTHER INFORMATION: Synthetic construct

<400> SEQUENCE: 25
ttgtggccgt ttacgtcgcc gtccagctcg accaggatgg gcaccacccc 50

<210> SEQ ID NO 26
<211> LENGTH: 51
<212> TYPE: DNA
<213> ORGANISM: Artificial Sequence
<220> FEATURE:
<223> OTHER INFORMATION: Synthetic construct

<400> SEQUENCE: 26
gagctggacg gcgacgtaaa cggccacaag ttcagcgtgt ccggcgaggg c 51

<210> SEQ ID NO 27
<211> LENGTH: 45
<212> TYPE: DNA
<213> ORGANISM: Artificial Sequence
<220> FEATURE:
<223> OTHER INFORMATION: Synthetic construct

<400> SEQUENCE: 27
ttgccgtagg tggcatcgcc ctcgccctcg ccggacacgc tgaac 45

<210> SEQ ID NO 28
<211> LENGTH: 48
<212> TYPE: DNA
<213> ORGANISM: Artificial Sequence
<220> FEATURE:
<223> OTHER INFORMATION: Synthetic construct

<400> SEQUENCE: 28
gagggcgatg ccacctacgg caagctgacc ctgaagttca tctgcacc 48

<210> SEQ ID NO 29
<211> LENGTH: 48
<212> TYPE: DNA
<213> ORGANISM: Artificial Sequence
<220> FEATURE:
<223> OTHER INFORMATION: Synthetic construct

<400> SEQUENCE: 29
cagggcacgg gcagcttgcc ggtggtgcag atgaacttca gggtcagc 48

<210> SEQ ID NO 30
<211> LENGTH: 54
<212> TYPE: DNA

<213> ORGANISM: Artificial Sequence
<220> FEATURE:
<223> OTHER INFORMATION: Synthetic construct

<400> SEQUENCE: 30
accggcaagc tgcccgtgcc ctggcccacc ctcgtgacca ccctgaccta cggc    54

<210> SEQ ID NO 31
<211> LENGTH: 55
<212> TYPE: DNA
<213> ORGANISM: Artificial Sequence
<220> FEATURE:
<223> OTHER INFORMATION: Synthetic construct

<400> SEQUENCE: 31
ggggtagcgg ctgaagcact gcacgccgta ggtcagggtg gtcacgaggg tgggc    55

<210> SEQ ID NO 32
<211> LENGTH: 48
<212> TYPE: DNA
<213> ORGANISM: Artificial Sequence
<220> FEATURE:
<223> OTHER INFORMATION: Synthetic construct

<400> SEQUENCE: 32
gtgcagtgct tcagccgcta ccccgaccac atgaagcagc acgacttc    48

<210> SEQ ID NO 33
<211> LENGTH: 51
<212> TYPE: DNA
<213> ORGANISM: Artificial Sequence
<220> FEATURE:
<223> OTHER INFORMATION: Synthetic construct

<400> SEQUENCE: 33
gtagccttcg ggcatggcgg acttgaagaa gtcgtgctgc ttcatgtggt c    51

<210> SEQ ID NO 34
<211> LENGTH: 51
<212> TYPE: DNA
<213> ORGANISM: Artificial Sequence
<220> FEATURE:
<223> OTHER INFORMATION: Synthetic construct

<400> SEQUENCE: 34
ttcaagtccg ccatgcccga aggctacgtc caggagcgca ccatcttctt c    51

<210> SEQ ID NO 35
<211> LENGTH: 49
<212> TYPE: DNA
<213> ORGANISM: Artificial Sequence
<220> FEATURE:
<223> OTHER INFORMATION: Synthetic construct

<400> SEQUENCE: 35
gggtcttgta gttgccgtcg tccttgaaga agatggtgcg ctcctggac    49

<210> SEQ ID NO 36
<211> LENGTH: 48
<212> TYPE: DNA
<213> ORGANISM: Artificial Sequence
<220> FEATURE:
<223> OTHER INFORMATION: Synthetic construct

<400> SEQUENCE: 36
aaggacgacg gcaactacaa gacccgcgcc gaggtgaagt tcgagggc    48

```
<210> SEQ ID NO 37
<211> LENGTH: 49
<212> TYPE: DNA
<213> ORGANISM: Artificial Sequence
<220> FEATURE:
<223> OTHER INFORMATION: Synthetic construct

<400> SEQUENCE: 37
agctcgatgc ggttcaccag ggtgtcgccc tcgaacttca cctcggcgc            49

<210> SEQ ID NO 38
<211> LENGTH: 51
<212> TYPE: DNA
<213> ORGANISM: Artificial Sequence
<220> FEATURE:
<223> OTHER INFORMATION: Synthetic construct

<400> SEQUENCE: 38
gacaccctgg tgaaccgcat cgagctgaag ggcatcgact caaggagga c          51

<210> SEQ ID NO 39
<211> LENGTH: 51
<212> TYPE: DNA
<213> ORGANISM: Artificial Sequence
<220> FEATURE:
<223> OTHER INFORMATION: Synthetic construct

<400> SEQUENCE: 39
tccagcttgt gccccaggat gttgccgtcc tccttgaagt cgatgccctt c          51

<210> SEQ ID NO 40
<211> LENGTH: 51
<212> TYPE: DNA
<213> ORGANISM: Artificial Sequence
<220> FEATURE:
<223> OTHER INFORMATION: Synthetic construct

<400> SEQUENCE: 40
ggcaacatcc tggggcacaa gctggagtac aactacaaca gccacaacgt c          51

<210> SEQ ID NO 41
<211> LENGTH: 52
<212> TYPE: DNA
<213> ORGANISM: Artificial Sequence
<220> FEATURE:
<223> OTHER INFORMATION: Synthetic construct

<400> SEQUENCE: 41
gttcttctgc ttgtcggcca tgatatagac gttgtggctg ttgtagttgt ac         52

<210> SEQ ID NO 42
<211> LENGTH: 51
<212> TYPE: DNA
<213> ORGANISM: Artificial Sequence
<220> FEATURE:
<223> OTHER INFORMATION: Synthetic construct

<400> SEQUENCE: 42
tatatcatgg ccgacaagca gaagaacggc atcaaggtga acttcaagat c          51

<210> SEQ ID NO 43
<211> LENGTH: 50
<212> TYPE: DNA
<213> ORGANISM: Artificial Sequence
<220> FEATURE:
```

<223> OTHER INFORMATION: Synthetic construct

<400> SEQUENCE: 43
acgctgccgt cctcgatgtt gtggcggatc ttgaagttca ccttgatgcc          50

<210> SEQ ID NO 44
<211> LENGTH: 49
<212> TYPE: DNA
<213> ORGANISM: Artificial Sequence
<220> FEATURE:
<223> OTHER INFORMATION: Synthetic construct

<400> SEQUENCE: 44
cgccacaaca tcgaggacgg cagcgtgcag ctcgccgacc actaccagc           49

<210> SEQ ID NO 45
<211> LENGTH: 51
<212> TYPE: DNA
<213> ORGANISM: Artificial Sequence
<220> FEATURE:
<223> OTHER INFORMATION: Synthetic construct

<400> SEQUENCE: 45
acggggccgt cgccgatggg ggtgttctgc tggtagtggt cggcgagctg c        51

<210> SEQ ID NO 46
<211> LENGTH: 51
<212> TYPE: DNA
<213> ORGANISM: Artificial Sequence
<220> FEATURE:
<223> OTHER INFORMATION: Synthetic construct

<400> SEQUENCE: 46
agaacacccc catcggcgac ggccccgtgc tgctgcccga caaccactac c        51

<210> SEQ ID NO 47
<211> LENGTH: 49
<212> TYPE: DNA
<213> ORGANISM: Artificial Sequence
<220> FEATURE:
<223> OTHER INFORMATION: Synthetic construct

<400> SEQUENCE: 47
tttgctcagg gcggactggg tgctcaggta gtggttgtcg ggcagcagc           49

<210> SEQ ID NO 48
<211> LENGTH: 50
<212> TYPE: DNA
<213> ORGANISM: Artificial Sequence
<220> FEATURE:
<223> OTHER INFORMATION: Synthetic construct

<400> SEQUENCE: 48
tgagcaccca gtccgccctg agcaaagacc ccaacgagaa gcgcgatcac          50

<210> SEQ ID NO 49
<211> LENGTH: 51
<212> TYPE: DNA
<213> ORGANISM: Artificial Sequence
<220> FEATURE:
<223> OTHER INFORMATION: Synthetic construct

<400> SEQUENCE: 49
ggcggtcacg aactccagca ggaccatgtg atcgcgcttc tcgttggggt c        51

```
<210> SEQ ID NO 50
<211> LENGTH: 51
<212> TYPE: DNA
<213> ORGANISM: Artificial Sequence
<220> FEATURE:
<223> OTHER INFORMATION: Synthetic construct

<400> SEQUENCE: 50
atggtcctgc tggagttcgt gaccgccgcc gggatcactc tcggcatgga c          51

<210> SEQ ID NO 51
<211> LENGTH: 49
<212> TYPE: DNA
<213> ORGANISM: Artificial Sequence
<220> FEATURE:
<223> OTHER INFORMATION: Synthetic construct

<400> SEQUENCE: 51
ggcggccgct ttacttgtac agctcgtcca tgccgagagt gatcccggc             49

<210> SEQ ID NO 52
<211> LENGTH: 20
<212> TYPE: DNA
<213> ORGANISM: Artificial Sequence
<220> FEATURE:
<223> OTHER INFORMATION: Synthetic construct

<400> SEQUENCE: 52
gagacgactc ctaatcgaac                                             20

<210> SEQ ID NO 53
<211> LENGTH: 20
<212> TYPE: DNA
<213> ORGANISM: Artificial Sequence
<220> FEATURE:
<223> OTHER INFORMATION: Synthetic construct

<400> SEQUENCE: 53
ccatcacgct gagtcttacg                                             20
```